United States Patent
Ikeda

(10) Patent No.: US 7,288,116 B2
(45) Date of Patent: Oct. 30, 2007

(54) HUCKLEBONE SUPPORTING-TYPE ARTIFICIAL LEG

(76) Inventor: Isao Ikeda, 573-167, Oazakituregawa, Kituregawamachi, Shioya-gun, Tochigi-ken 329-1412 (JP)

( * ) Notice: Subject to any disclaimer, the term of this patent is extended or adjusted under 35 U.S.C. 154(b) by 188 days.

(21) Appl. No.: 11/134,623

(22) Filed: May 23, 2005

(65) Prior Publication Data

US 2005/0278038 A1    Dec. 15, 2005

(30) Foreign Application Priority Data

Jun. 11, 2004    (JP)    .............................. 2004-173556

(51) Int. Cl.
*A61F 2/60*    (2006.01)
(52) U.S. Cl. .......................... 623/28; 623/31
(58) Field of Classification Search ............. 623/27–32
See application file for complete search history.

(56) References Cited

U.S. PATENT DOCUMENTS

| | | |
|---|---|---|
| 1,082,256 A | 12/1913 | Apgar |
| 1,299,980 A * | 4/1919 | Marcinko .................... 623/31 |
| 2,008,897 A | 7/1935 | Carnes |
| 3,272,210 A | 9/1966 | Boruvka |
| 4,697,808 A | 10/1987 | Larson et al. |
| 5,230,700 A | 7/1993 | Humbert et al. |
| 5,482,070 A | 1/1996 | Kelly |
| 5,529,576 A | 6/1996 | Lundt et al. |

* cited by examiner

*Primary Examiner*—Bruce Snow

(57) ABSTRACT

This invention relates to enable a person to walk smoothly even if a length of a remained thigh of the lost leg is short or even if the leg is cut at the hip joint and has no thigh. The hucklebone supporting type artificial leg comprising the crotch support (1), the shaft part (21) arranged vertically at the lower surface of the crotch support (1) and having substantially the same length as that of the lower leg and a foot (22) fixed to the lower end of the shaft part (21), wherein the crotch support (1) is formed into a substantial L-shape as seen in its top plan view, one front end (2) is arranged at a front part so as to be applied to a substantial front half part of the crotch part when installed and at the same time, the other side end part (3) is arranged at the rear surface of the lost lower leg and applied to both the hucklebone and the hip part corresponding to the lost leg when installed. The front band supporting unit (41) and the rear band supporting unit (42) are arranged at the front and rear ends of the crotch support (1) in such a way that they can be turned around and there are provided waist bands (43), (44) and shoulder hanging band (47).

8 Claims, 28 Drawing Sheets

HUCKLEBONE SUPPORTING-TYPE ARTIFICIAL LEG

BACKGROUND OF INVENTION

1. Technical Field

This invention relates to a hucklebone supporting-type artificial leg in which a crotch support is arranged at the upper end of an artificial leg, and applied to the crotch part to support a person's weight with the hucklebone.

2. Background Art

As the prior art hucklebone artificial leg in which a saddle is arranged at the upper end of the artificial leg to support person's weight with the hucklebone while being applied to the crotch portion of a person and to fix a left thigh portion at the lost lower leg side, there have been provided "Artificial Leg" described in the Patent Document 1 and "Saddle-Type Crutch" described in the Patent Document 2. Since the saddle is abutted against the crotch to support weight of a person, these units enabled the person to wear an artificial leg and walk at an early stage where the wounded portion is not yet completely healed when the lower leg is damaged, lost or wounded due to accident, explosion of mine and illness or the like. In addition, these units enabled a mass production and a low price product to be provided due to no necessity to make it under an order-made basis in compliance with a shape of the damaged portion of the lost lower leg as found in the prior art artificial leg.

Patent Document 1:
Gazette of Japanese Design Registration No. 1,163,891
Patent Document 2:
Gazette of Japanese Patent Laid-Open No. 2002-34717

DISCLOSURE OF THE INVENTION

As described above, the hucklebone supporting-type artificial leg provides a comfortable wearing touch due to no application of load at the extremity end of the lost lower leg, provides no necessity of making a special walking training and enables the artificial leg wearing person to walk just after wearing it. However, looking from the front at an attitude of a person wearing the prior art hucklebone supporting-type artificial leg shows that at a normal lower leg side a physical weight applied on the lower leg is supported with the crotch joint of the end part of the pelvis. However, due to wearing of the artificial leg, at the lost lower leg side a physical weight applied to the lower leg is supported with the hucklebone of the crotch through the saddle, i.e. at a central position in a lateral direction. As a result, the attitude supporting the upper physical body shows an unbalanced state, the person may easily take an attitude where the upper physical body is moved toward the normal lower leg and the attitude of the upper physical body during walking may easily be disordered.

In addition, when a length of the thigh portion left at the lost lower leg side is short, the prior art hucklebone supporting-type artificial leg shows a disadvantage that a fixing between the artificial leg and the thigh portion is not sufficiently performed. Additionally, when the lower leg is cut at the crotch joint part and has no thigh portion, the artificial leg cannot be fixed to the thigh portion. In these cases, there occurred a problem that a fixing of the artificial leg to the physical body becomes insufficient, and an action for pulling up the rear artificial leg and moving it in a forward direction cannot be performed smoothly during walking.

Additionally, the prior art hucklebone supporting-type artificial leg shows that, when a person walks while the artificial leg is being fixed to the thigh portion at the lost lower leg side, the foot portion moves forward or rearward like a pendulum around the saddle part of the crotch portion in reference to the motion of the foot at the extremity end of the artificial leg. In this case, a swinging angle of the foot portion in a forward and upward direction and a swinging angle of the foot portion in a rearward and upward direction are substantially equal to each other. In turn, a motion of the thigh portion at the normal lower leg side not wearing any artificial leg shows that the thigh portion has a large forward and upward swinging angle due to a presence of the knee joint and correspondingly it shows a low rearward swinging angle. As described above, a movable range at the artificial leg side is displaced more in a rearward direction as compared with that of the thigh portion at the normal leg side, resulting in that the thigh portion at the lost leg side is forcedly caused to incline in a rearward direction which could not be produced during walking under the normal state. As a result, when the thigh portion is left rearward during walking and the artificial leg is inclined rearward, the pelvis is also inclined concurrently, the upper half physical body is inclined forward or twisted and a walking attitude is disturbed.

In view of the foregoing, it is an object of the present invention to provide a hucklebone supporting-type artificial leg in which a lateral unbalanced physical weight applied to the artificial leg is reduced more to improve a wearing touch into a more comfortable state. In addition, it is an object of the present invention to provide the hucklebone supporting-type artificial leg capable of positively fixing the artificial leg to the hucklebone even if the left thigh portion at the lost lower leg side is short in its length or no thigh portion is present. Further, it is an object of the present invention to provide the hucklebone supporting-type artificial leg capable of performing a more smooth operation when the artificial leg is moved forward or rearward during walking and further capable of reducing a disturbance in a wearing person's attitude.

In order to solve the above problems, this invention is characterized as follows.

A hucklebone supporting-type artificial leg comprising a crotch support, a shaft vertically arranged at the lower surface of said crotch support and having substantially the same length as that of a lower leg and a foot attached to the lower end of said shaft characterized in that said crotch support is formed into a substantial L-shape as seen from its top plan view, one end side of said crotch support is arranged at a front part and applied to a substantial front half part of the crotch when installed and the other end side of said crotch support is arranged at a back part at the lost lower leg side and applied to both the hucklebone and the hip at the lost lower leg side when installed.

The hucklebone supporting-type artificial leg is characterized in that said crotch support has both ends raised.

The hucklebone supporting-type artificial leg is characterized in that said shaft is vertically arranged at the lower surface of an intermediate bent part of said crotch support and said shaft is offset to a slant front part at the lost lower leg side.

The hucklebone supporting-type artificial leg is characterized by comprising a front band supporting unit attached to the front end of said crotch support in such a way that it can be turned in front, upward and downward directions; a rear band supporting unit attached to the rear end of an intermediate bent part of said crotch support in such a way that it can be turned in rear, upward and downward directions; and a waist band connected to each of the upper ends of said front and rear band supporting units and installed around the waist of an artificial leg wearing person in such a way that it can be fastened, fixed or removed.

The hucklebone supporting-type artificial leg is characterized by comprising a shoulder hanging band of which end is connected to each of the upper ends of said front and rear band supporting units and which is installed on the shoulder of an artificial leg wearing person in such a way that it can be fastened, fixed or removed.

The hucklebone supporting-type artificial leg is characterized in that said crotch support is formed into a lateral symmetrical shape, said front band supporting unit can be removably installed at both ends of said crotch support, said rear band supporting unit can be installed on a person having the right or left lost lower leg by enabling a fixing orientation at the rear end of the intermediate bent part of said crotch support to be turned around a vertical axis.

The hucklebone supporting-type artificial leg is characterized in that there is provided a concave-shaped thigh-abutting unit attached to the upper part of said shaft in a slant forward and downward direction to cause the thigh part at the lost lower leg side to be fixed by a fastening band.

The hucklebone supporting-type artificial leg is characterized in that a movable-up and -down cylinder is applied to cover said shaft at its middle part, the shaft in the cylinder at a position where said cylinder descends is divided into two upper and lower segments and the segments are connected by a hinge, the upper segment of said shaft can be inclined rearward under a state in which said cylinder is ascended.

The hucklebone supporting-type artificial leg is characterized in that an optional section of said shaft is formed into a double-shaft structure, a plurality of axially and properly spaced-apart holes are punched at said double-shaft structure section in a diameter-facing orientation, a pin is removably inserted into each of said holes to enable a length of said shaft to be adjusted in a stepwise manner.

The hucklebone supporting-type artificial leg is characterized in that said foot is connected to the lower end of said shaft at an intermediate position in a forward or rearward direction of the lower ground contact surface of said foot and also at a position offset to one of the right and left directions and at the same time the lower end of said shaft is inserted into or held at said foot, the foot part is fastened with a screw, and an offset direction of said foot in respect to the lower end of said shaft can be switched over in right and left sides.

As described above, in accordance with the present invention, a shape of the crotch support is formed into a substantial L-shape as seen in its top plan view, one end is abutted against the crotch, the other end is abutted against the hip portion at the lost lower leg side, thereby a wearing person's physical weight is supported with the hucklebone at the lost lower leg side when the weight is applied to the artificial leg side, a lateral unbalanced state for supporting the weight is improved, a wearing touch or feeling is improved and a more natural walk can be realized.

In addition, the upper portion of the shaft is offset from the connecting position of the crotch support toward a slant forward direction at the lost lower leg side to enable a stability of the artificial leg supporting the wearing person's weight to be increased and further a walking of the leg wearing person to be performed more smoothly.

Further, each of the front and rear band supporting units is fixed to the front and rear ends of the crotch support in such a way that its upward or downward turning operation can be performed, respectively, a waist band is connected to each of the upper ends of the front and rear band supporting units, respectively, it is installed around the waist of the artificial leg wearing person in such a way that it can be removably fastened, resulting in that the artificial leg wearing characteristic can be improved and a stable walking of the person can be carried out.

In addition, an installing characteristic of the artificial leg can be further improved and a stable walking of the person can be carried out by connecting the end part of the shoulder hanging band to the upper ends of the front and rear band supporting units and hunging the band at the shoulder of the artificial leg wearing person to support the crotch support.

In addition, the artificial leg can be installed at a person with either right or left lower leg being lost by making a shape of the crotch support in a lateral symmetrical one, enabling the fixing positions of the front and rear band supporting units to be changed over to right and left and further enabling the offset orientation of the foot to be changed over to right and left.

In addition, a walking stability is improved by arranging the thigh-abutting part to the upper part of the shaft in a slant forward, downward direction and fixing the thigh portion at the lost lower leg side.

In addition, arrangement of the hinge at a middle part of the shaft enables an artificial leg wearing person to take a seat while the artificial leg is being installed.

Additionally, a length of the shaft can be adjusted in a stepwise manner to enable one type of artificial leg to be adapted for the physical size of the wearing person.

The present invention can be temporarily used in place of the crutch when one leg cannot support a physical weight due to a fracture of bone or an injury other than its utilization as an artificial leg when a lower leg is lost due to accident, explosion of mine and illness or the like.

BEST MODE FOR CARRYING OUT THE INVENTION

Figure 1:
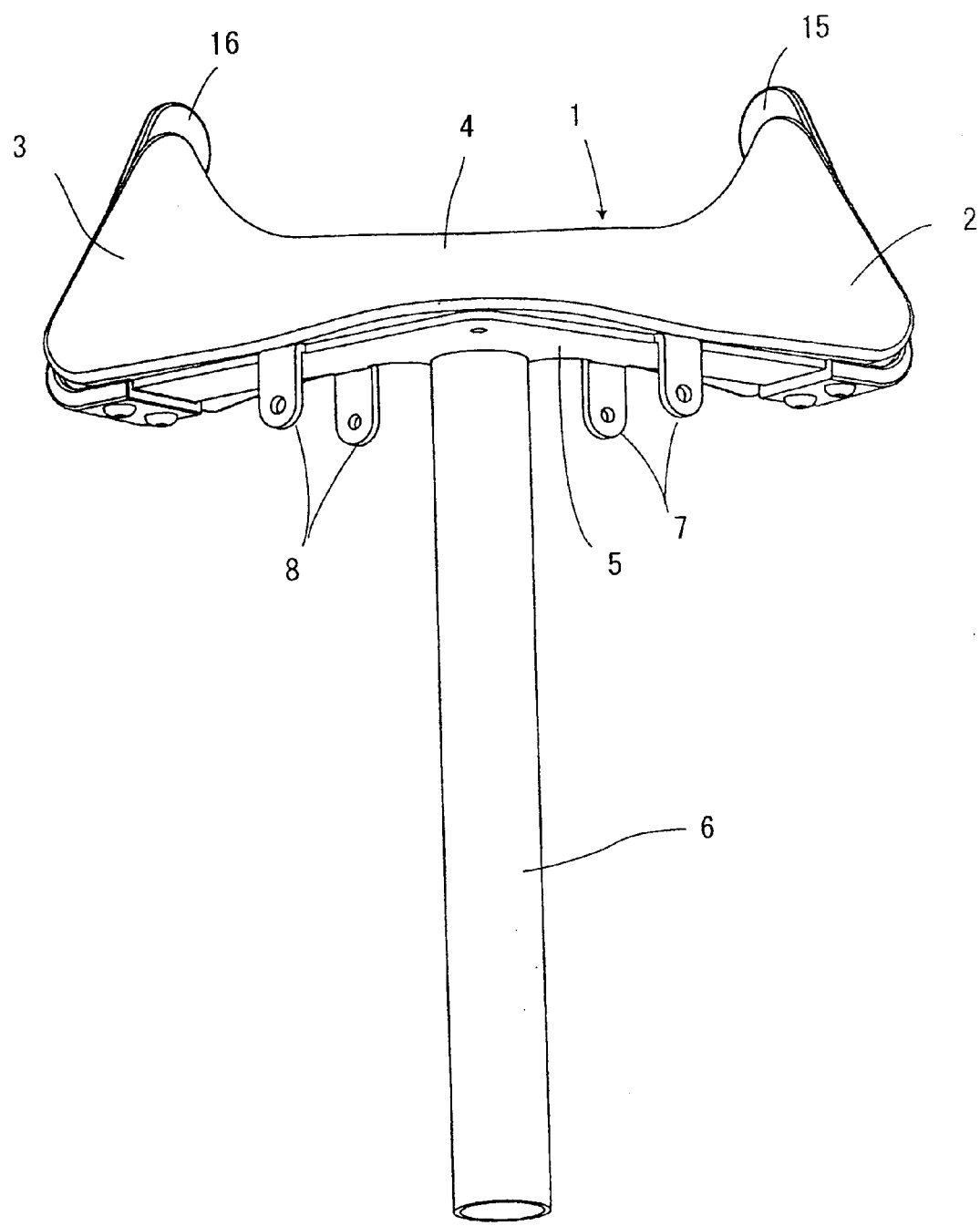
FIG. 1 is a perspective view of a crotch support of the hucklebone supporting-type artificial leg of the present invention as seen from a slant rearward direction.

Referring now to the drawings, one preferred embodiment of the present invention will be described as follows. Although the hucklebone supporting-type artificial leg to be described in the preferred embodiment is constituted in a lateral symmetrical manner and can be changed over and installed while the lost lower leg is any one of right and left legs, a case in which the artificial leg is installed on a wearing person having the lost left lower leg will be described.

Figure 2:
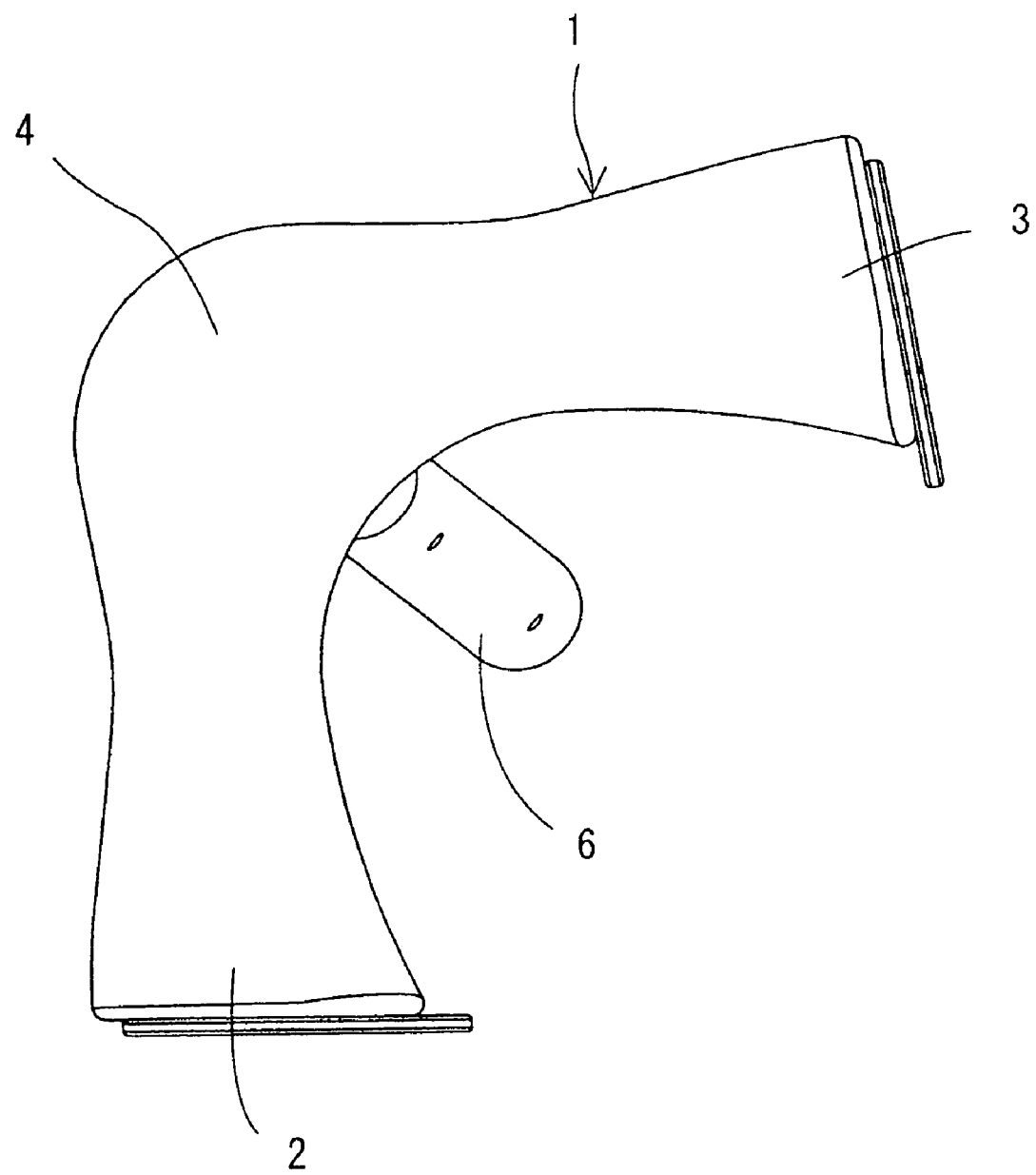
FIG. 2 is a top plan view for showing a crotch support of the hucklebone supporting-type artificial leg of the present invention.
Figure 3:
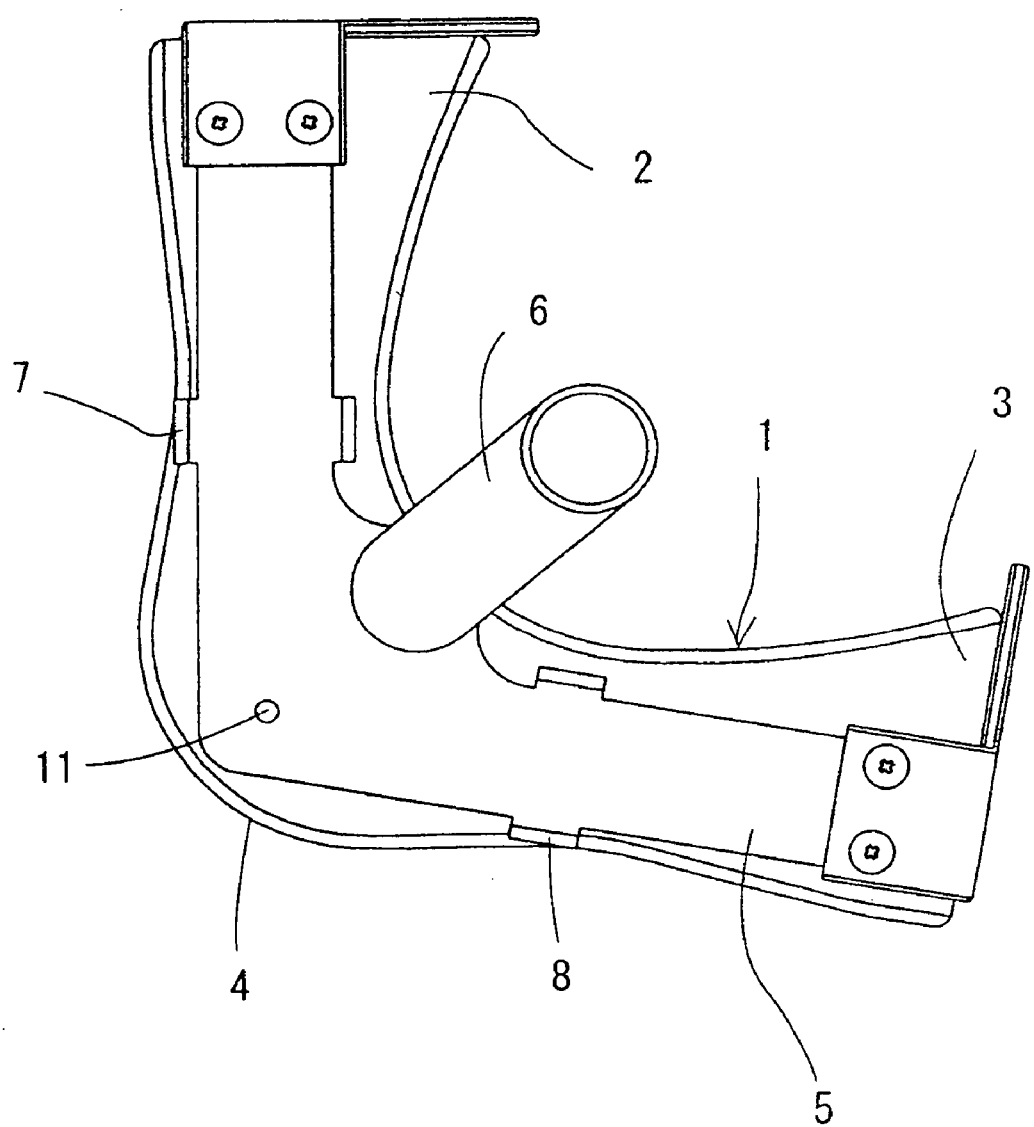
FIG. 3 is a bottom view for showing a crotch support of the hucklebone supporting-type artificial leg of the present invention.
Figure 4:
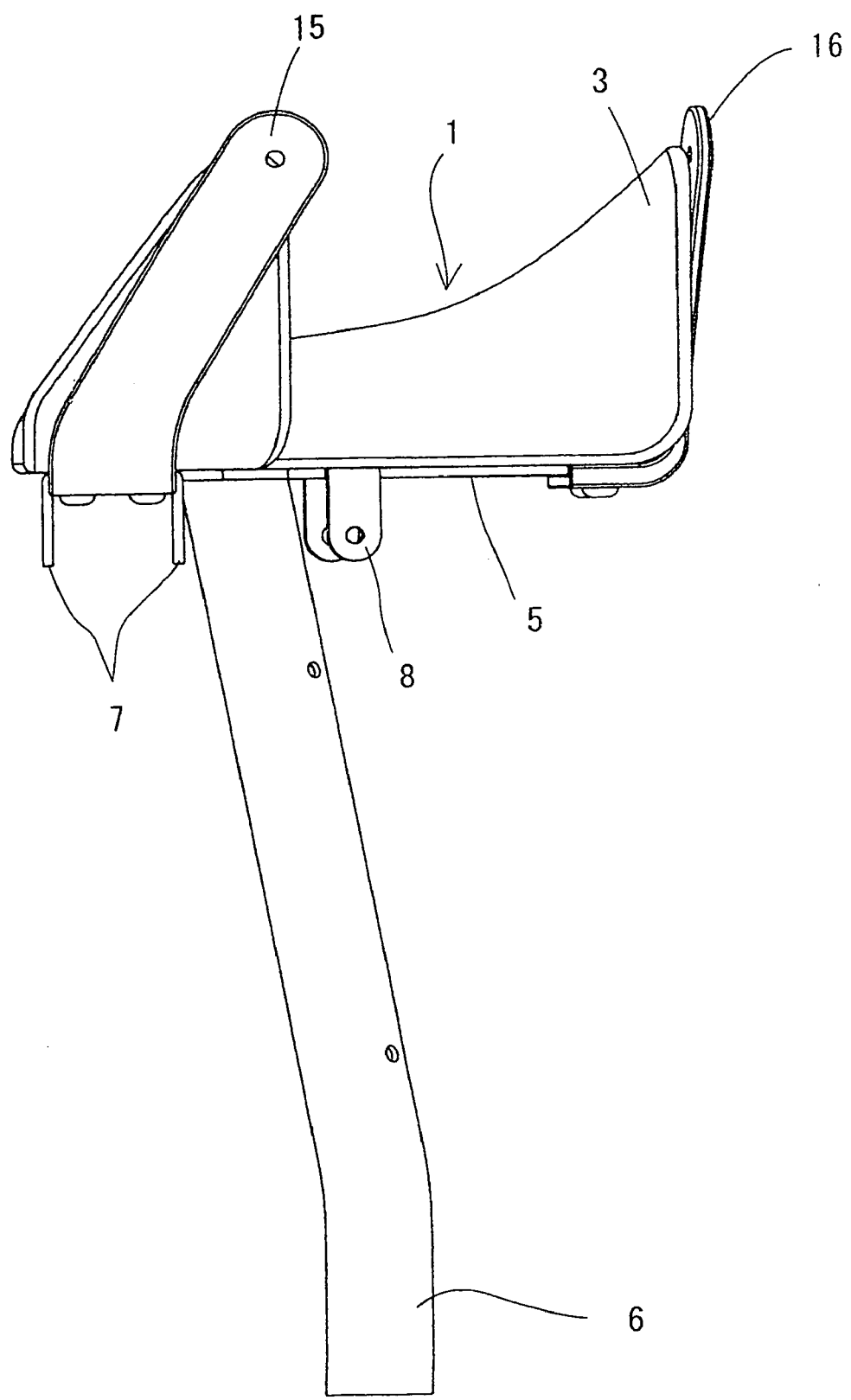
FIG. 4 is a front elevational view for showing a crotch support of the hucklebone supporting-type artificial leg of the present invention.
Figure 5:
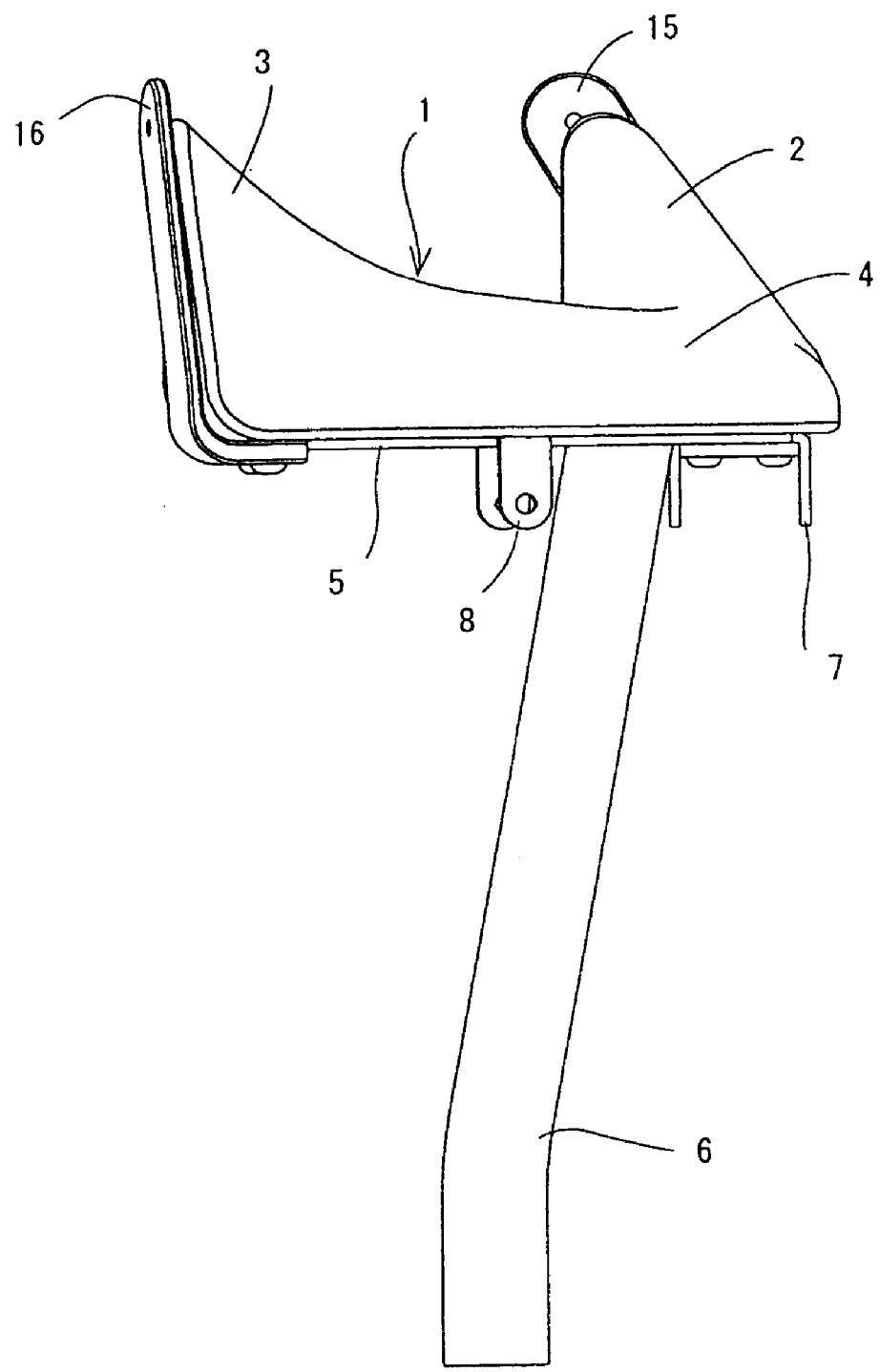
FIG. 5 is a rear view for showing a crotch support of the hucklebone supporting-type artificial leg of the present invention.
Figure 6:
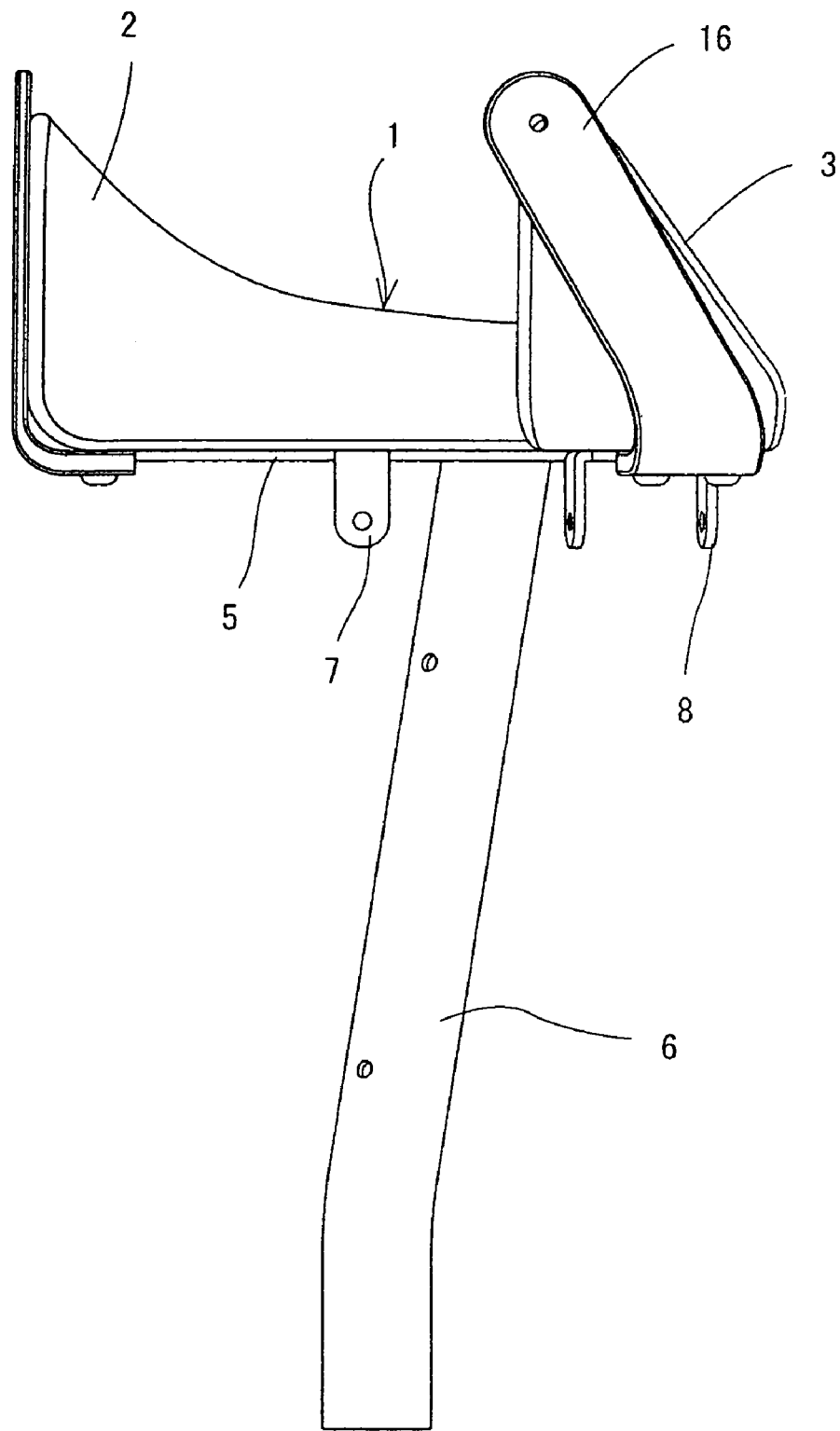
FIG. 6 is a right side elevational view for showing a crotch support of the hucklebone supporting-type artificial leg of the present invention.
Figure 7:
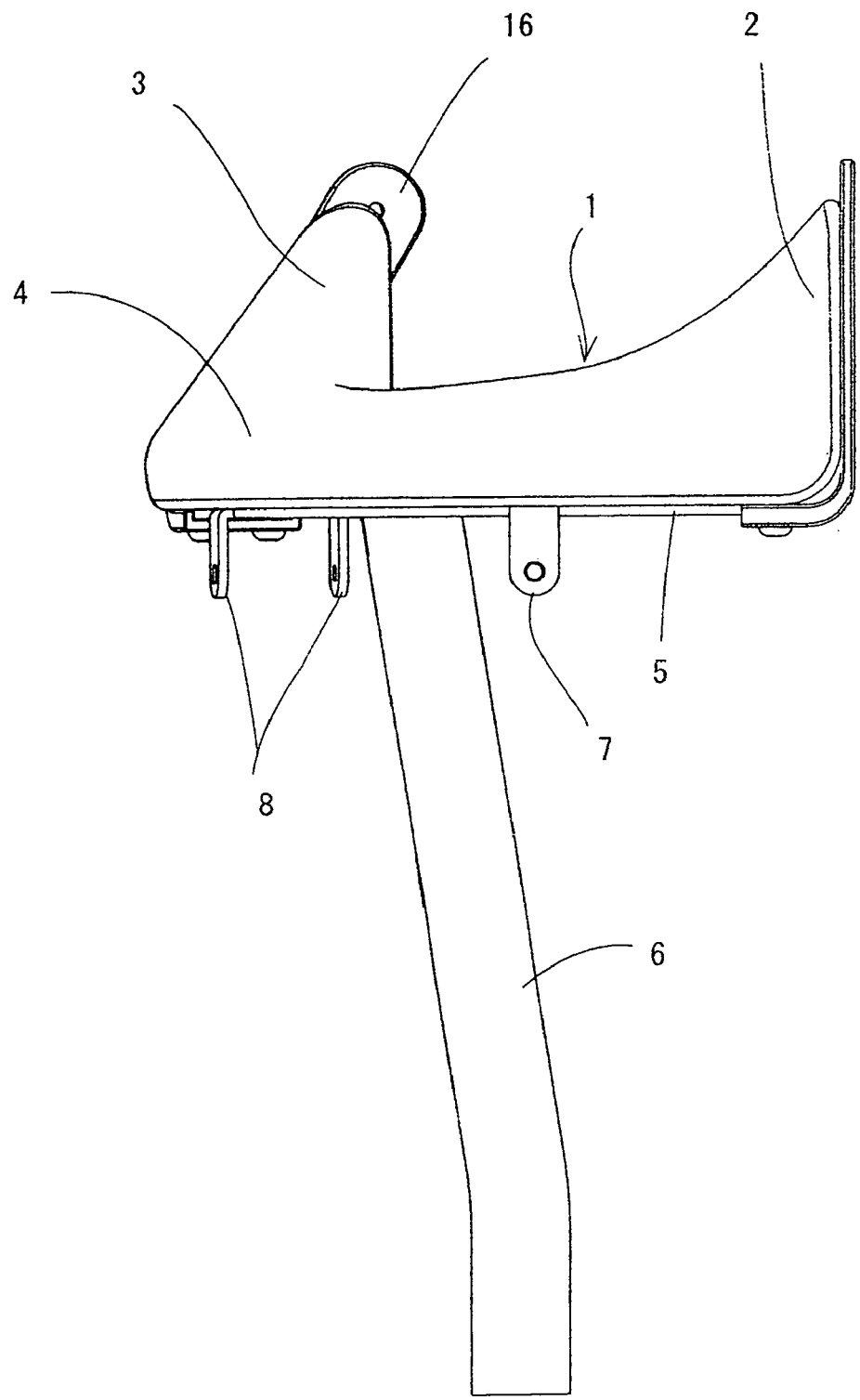
FIG. 7 is a left side elevational view for showing a crotch support of the hucklebone supporting-type artificial leg of the present invention.
Figure 8:
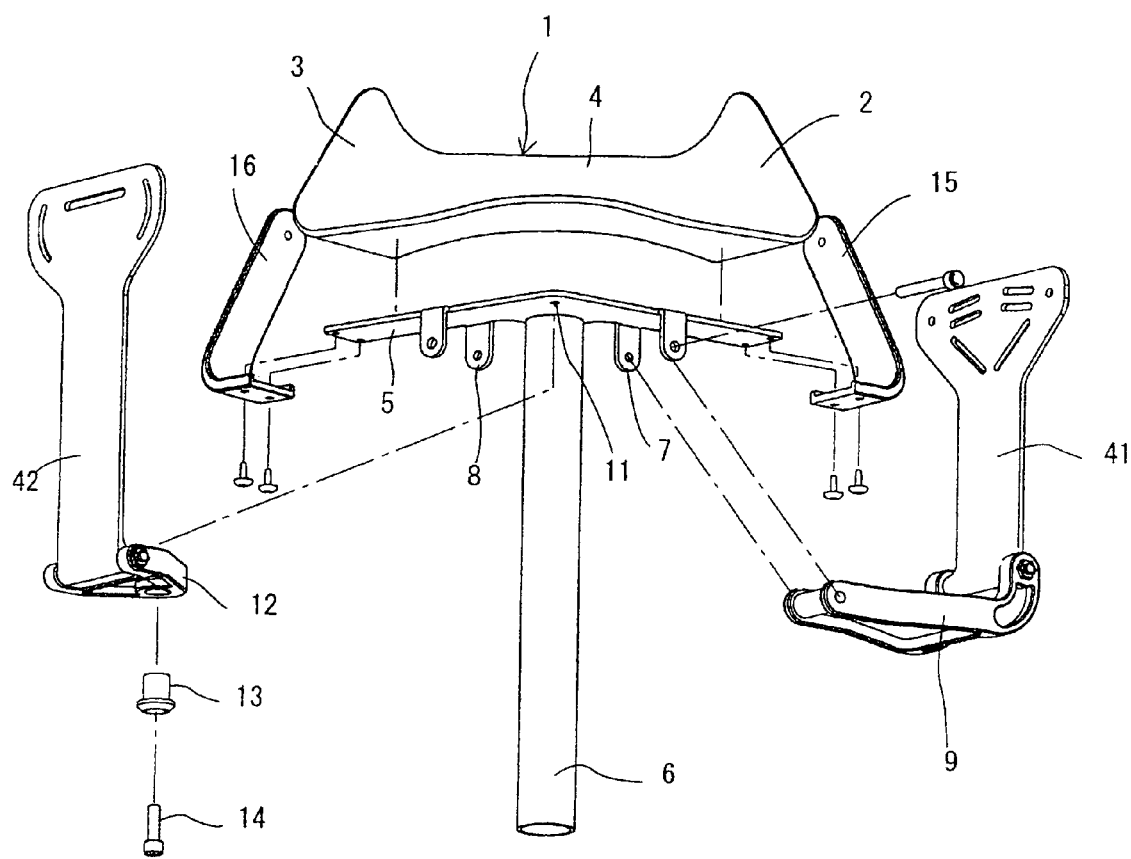
FIG. 8 is an exploded perspective view for showing a crotch support of the hucklebone supporting-type artificial leg of the present invention.

At first, a structure of the crotch support part will be described. FIGS. 1 to 8 illustrate separately the crotch support portion of the hucklebone supporting-type artificial leg of the present invention, wherein FIG. 1 is a perspective view of the crotch support as seen from a slant rear part, FIG. 2 is a top plan view, FIG. 3 is a bottom view, FIG. 4 is a front elevational view, FIG. 5 is a rear view, FIG. 6 is a right side elevational view, FIG. 7 is a left side elevational view and FIG. 8 is an exploded perspective view.

As shown in these figures, a crotch support 1 is formed into an L-shape as seen from its top plan view, its front end 2 and a side end 3 are slightly wide and raised. In addition, an intermediate bent part 4 is also formed into a slight wide shape. When a person wears the artificial leg, this front end 2 is abutted against the front half part of the crotch and at the same time the side end 3 is abutted against the left hip and the hucklebone at the lost lower leg side. Further, in the illustrated example, although a crossing angle between the front end 2 and the side end 3 is set to 100 degrees, this value is not limited to 100 degrees. To the bottom surface of the crotch support 1 is fastened a seat plate 5 of metallic plate for use in fixing the shaft, and a crotch support shaft 6 is vertically arranged at its central part. The crotch support shaft 6 is inclined in a slant forward direction where a crossing angle between the front end 2 and the side end 3 is divided into two segments and at the same time its lower end is bent in a direction perpendicular to the seat plate 5. That is, the lower end of the crotch support shaft 6 is offset from the base end of its upper end in a slant forward direction.

Each of a pair of brackets 7, 8 is protruded at an intermediate position between the front end 2 and the side end 3 of the seat plate 5, respectively, and then an L-shaped link fitting 9 is pivotally attached to fix a front band supporting unit 41 to be described later. As shown in FIG. 8, a threaded hole 11 is formed at an outside part of a base end of the crotch support shaft 6 at an intermediate location of the seat plate 5, and a fitting 12 for use in fixing a rear band supporting unit 42 to be described later is pivotally attached through a sleeve 13 by a small screw 14 in such a way that it can be turned. With this arrangement above, the fitting 12 can be turned around the pin 14 by about 100 degrees. Each of the connecting fittings 15, 16 having a metallic plate bent into an L-shape is fixed with a small screw to both ends of the seat plate 5, their upper portions are abutted against the end surface of the front end 2 and the end surface of the side end 3. A fastening band 32 attached to a thigh-abutting unit 31 to be described later is engaged with the upper ends of the connecting fittings 15, 16.

Figure 9:
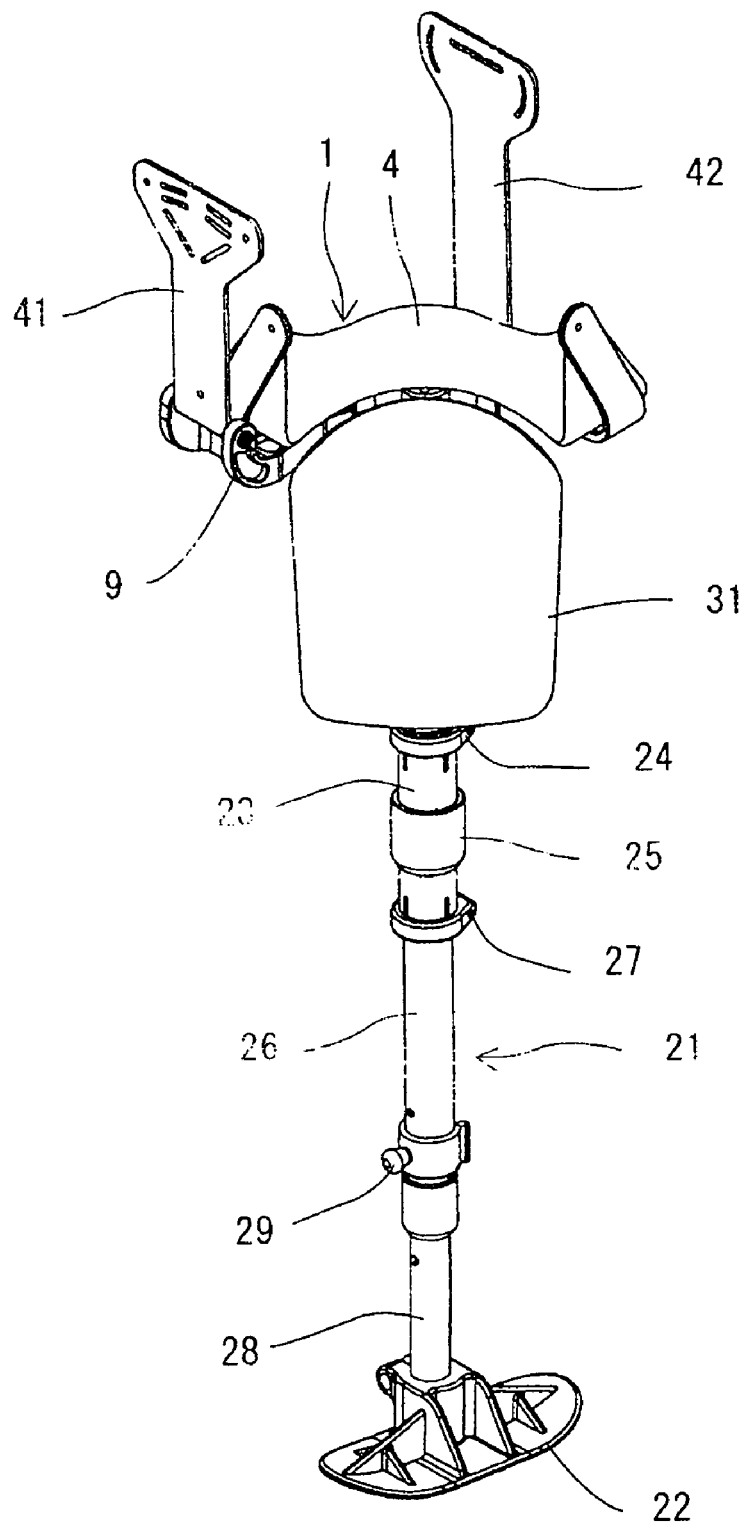
FIG. 9 is a perspective view for showing the hucklebone supporting-type artificial leg of the present invention during its assembling operation.
Figure 10:
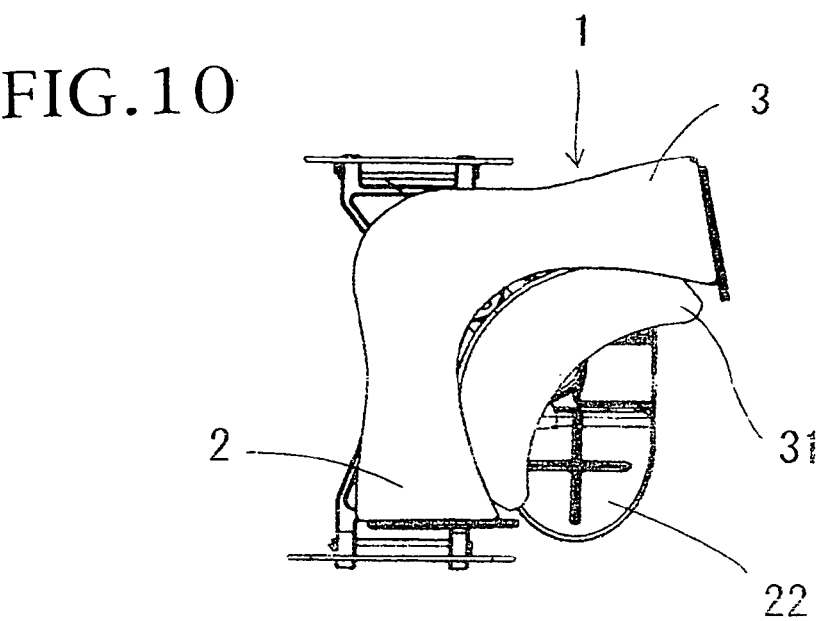
FIG. 10 is a top plan view for showing the hucklebone supporting-type artificial leg of the present invention during its assembling operation.
Figure 11:
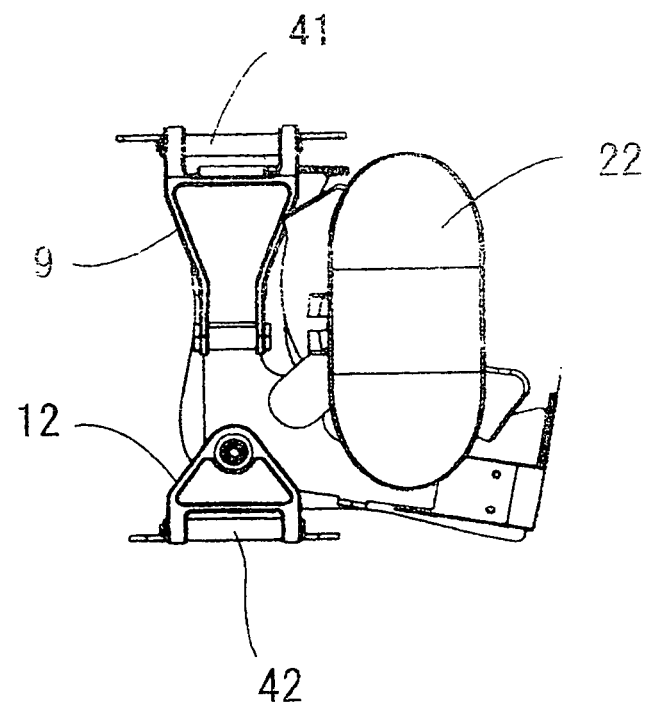
FIG. 11 is a bottom view for showing the hucklebone supporting-type artificial leg of the present invention during its assembling operation.
Figure 12:
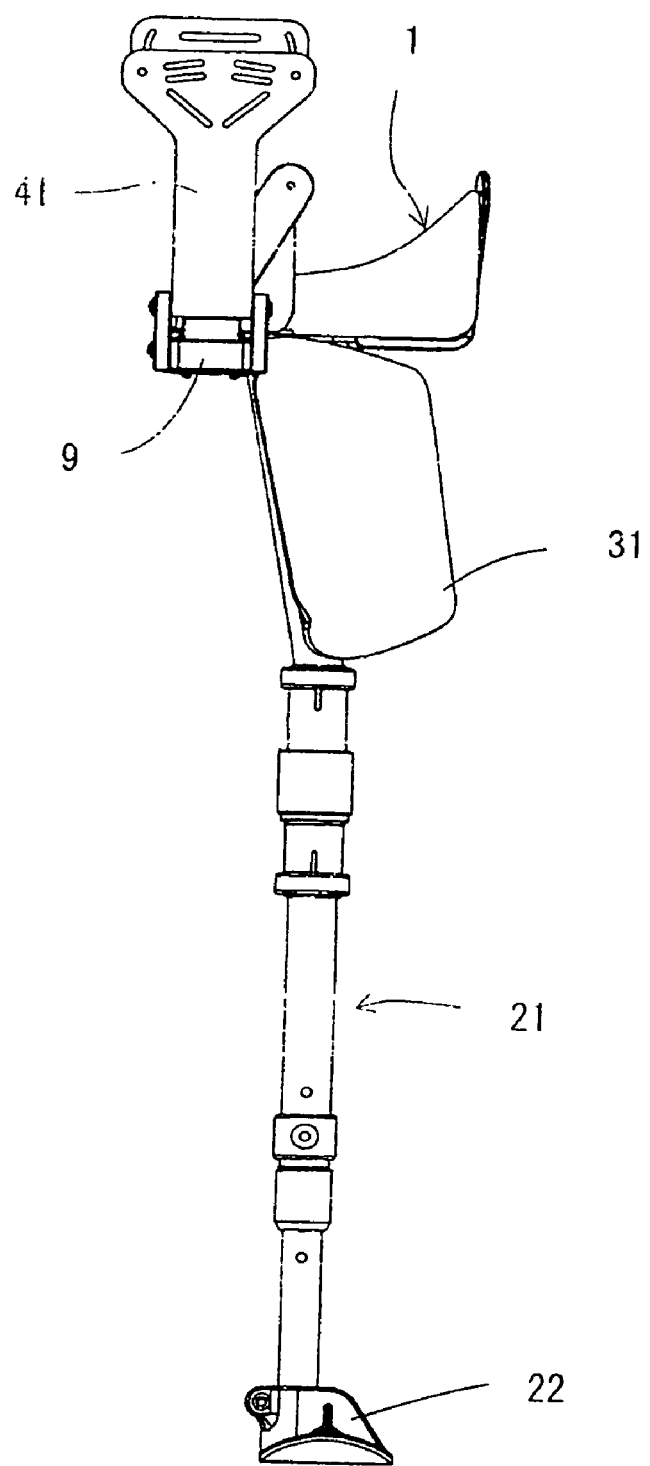
FIG. 12 is a front elevational view for showing the hucklebone supporting-type artificial leg of the present invention during its assembling operation.
Figure 13:
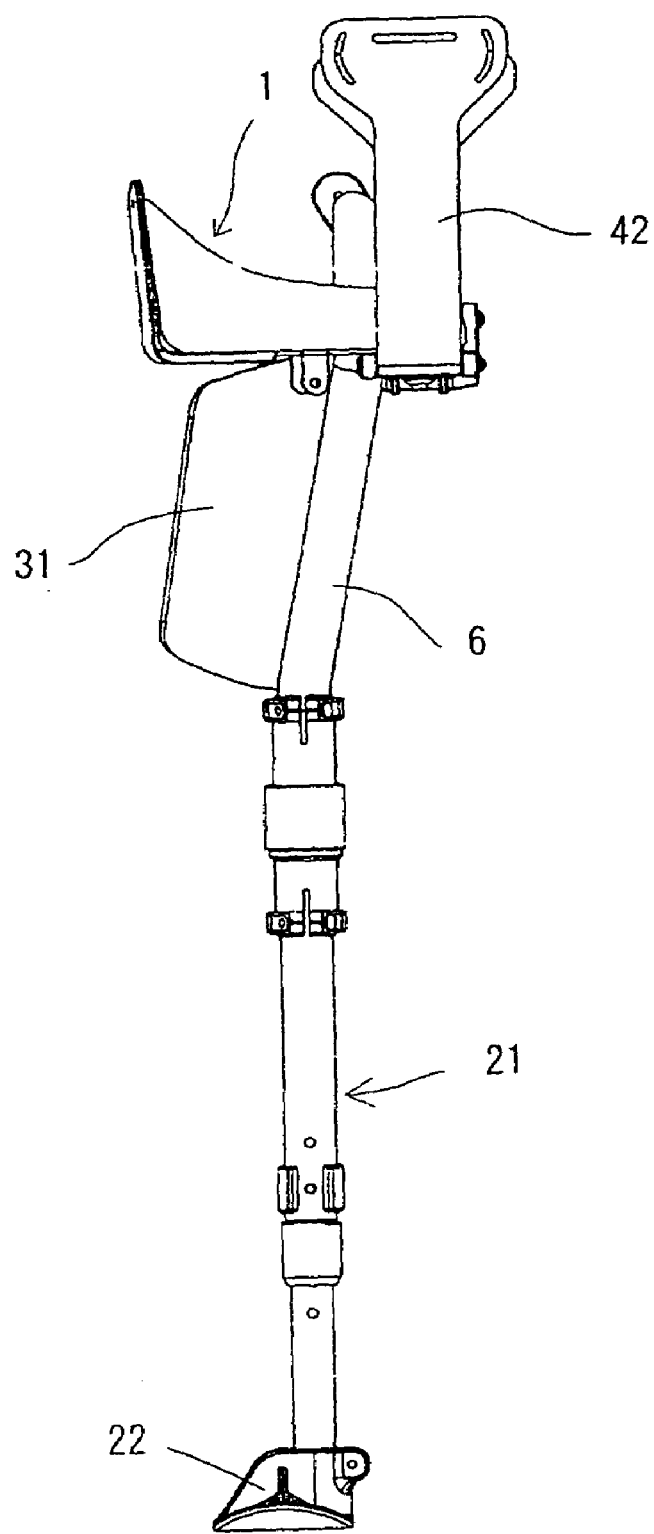
FIG. 13 is a rear view for showing the hucklebone supporting-type artificial leg of the present invention during its assembling operation.
Figure 14:
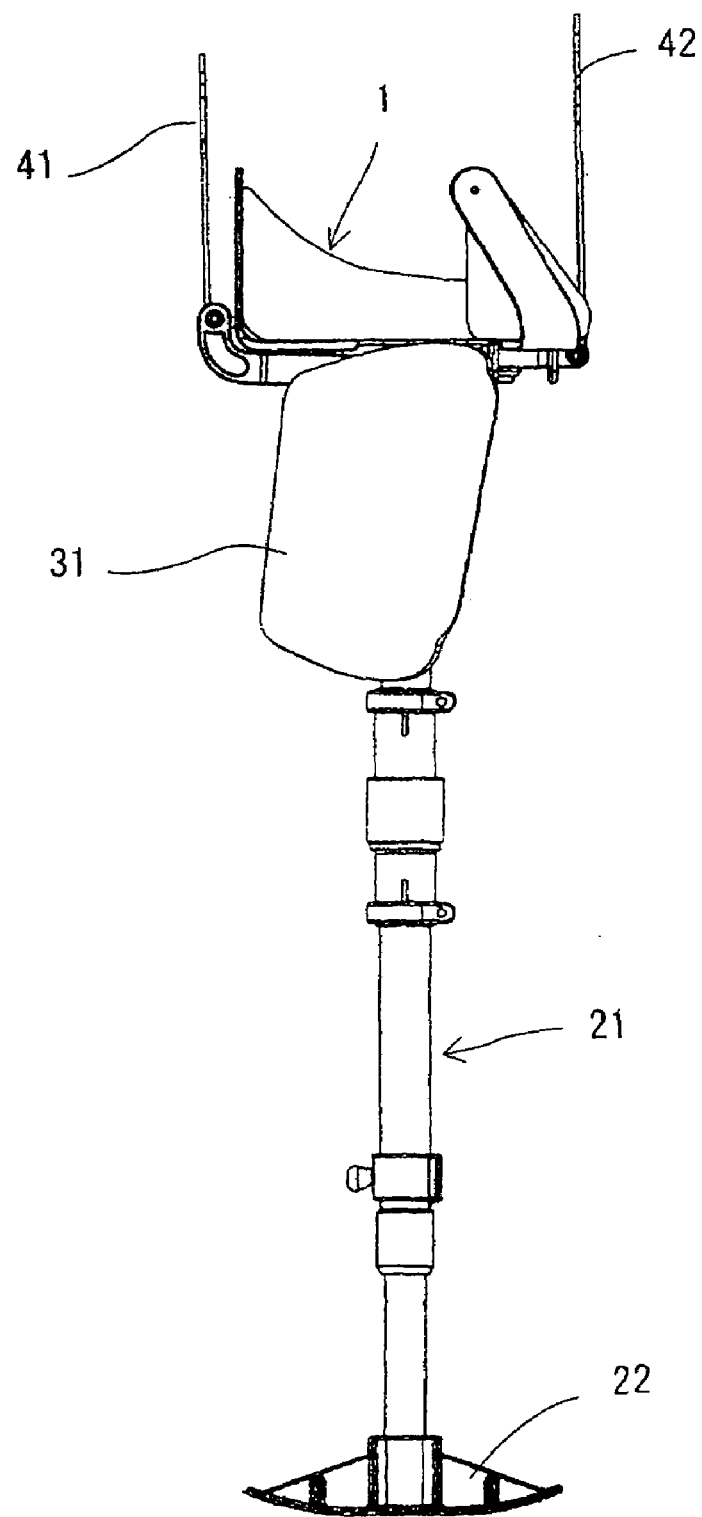
FIG. 14 is a right side elevational view for showing the hucklebone supporting type artificial leg of the present invention during its assembling operation.
Figure 15:
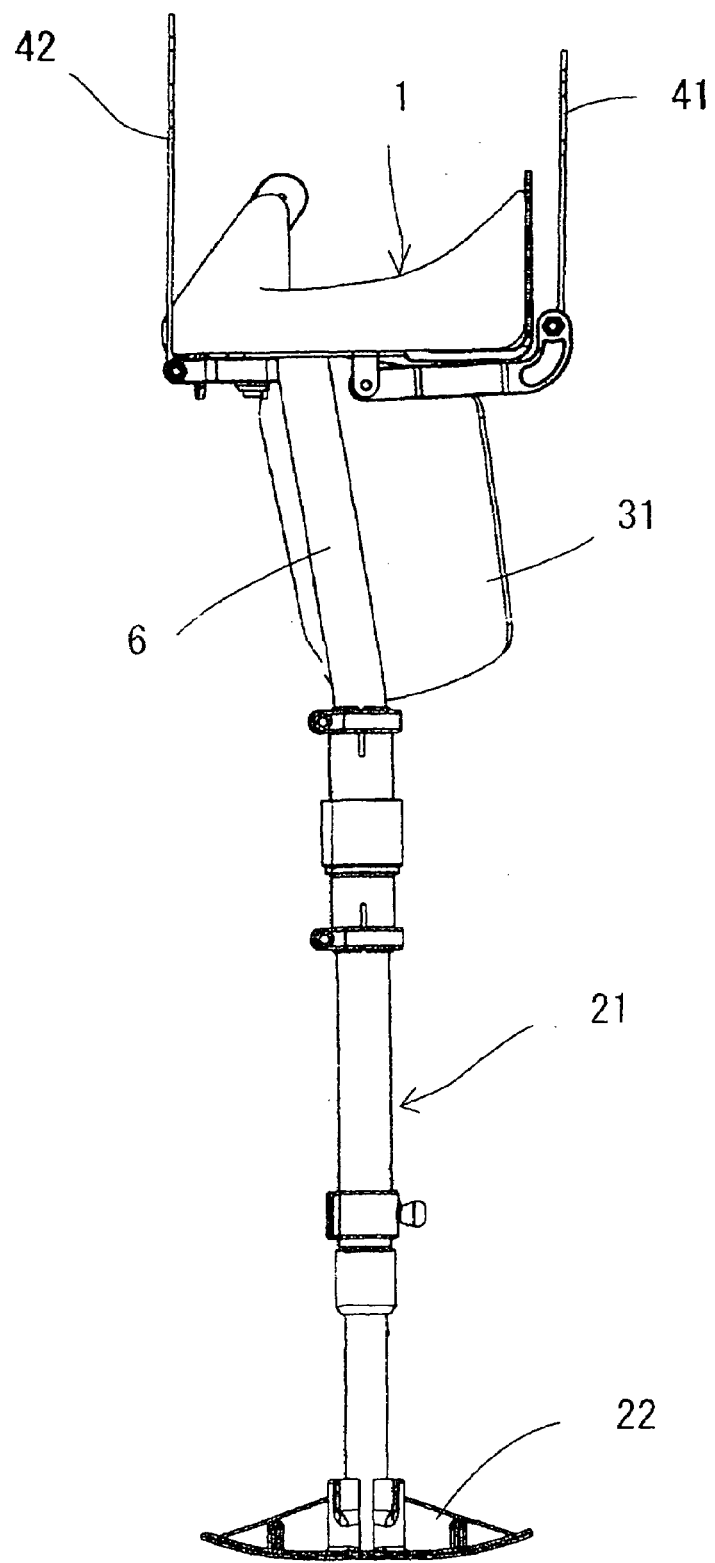
FIG. 15 is a left side elevational view for showing the hucklebone supporting type artificial leg of the present invention during its assembling operation.

Next, there will be described about the hucklebone supporting-type artificial leg during its assembling state in which the shaft, foot and front and rear band supporting units are fixed to the crotch support part. FIGS. 9 to 15 illustrate the hucklebone supporting-type artificial leg during its assembling state, FIG. 9 is a perspective view as seen from a slant front part, FIG. 10 is a top plan view, FIG. 11 is a bottom view, FIG. 12 is a front elevational view, FIG. 13 is a rear view, FIG. 14 is a right side elevational view and FIG. 15 is a left side elevational view. As shown in these figures, a shaft 21 is connected to the lower end of the crotch support shaft 6 and a foot 22 is fixed to the lower end of the shaft. The upper end of the shaft 21 comprises an upper shaft 23 and this is formed into a cylindrical shape to enable the crotch support shaft 6 to be inserted and at the same time, some slits are formed at its outer circumference, after the crotch support shaft 6 is inserted into it, its outside part is fastened with a slit collar 24 to enable the upper shaft 23 and the crotch support shaft 6 to be adjusted at an optional angle and connected to each other.

A collar 25 is fitted to the upper shaft 23 below the slit collar 24 in such a way that it can be ascended or descended, and a hinge structure to be described later is stored inside it. The lower end of the upper shaft 23 is connected while a middle shaft 26 is inserted inside it and its outside part is fastened with a slit collar 27. The middle shaft 26 has a hollow structure and a lower shaft 28 is inserted from the lower end, a clip pin 29 is pulled or inserted to enable its height to be adjusted. With such an arrangement as above, one type of artificial leg of the present invention can adapt for various types of physical state of the leg wearing person. The foot 22 having the lower end of the lower shaft 28 inserted therein is constructed such that its inserted part is formed with a slit and clamped by a small screw, and the fixing position of the foot 22 can be replaced for its right and left orientations.

To the crotch support shaft 6 abutting against the lower portion between the front end 2 and the side end 3 of the crotch support 1 is fixed the molded concave-shaped thigh-abutting unit 31 in parallel with the crotch support shaft 6. The front band supporting unit 41 connected to the end part of the L-shaped link fitting 9 is supported in front of the front end 2 in such a way that it can be turned in a forward or rearward direction. The rear band supporting unit 42 connected to the end part of the fitting 12 is supported at a rear part of the intermediate bent part 4 in such a way that it can be turned in a forward or rearward direction.

Figure 16:
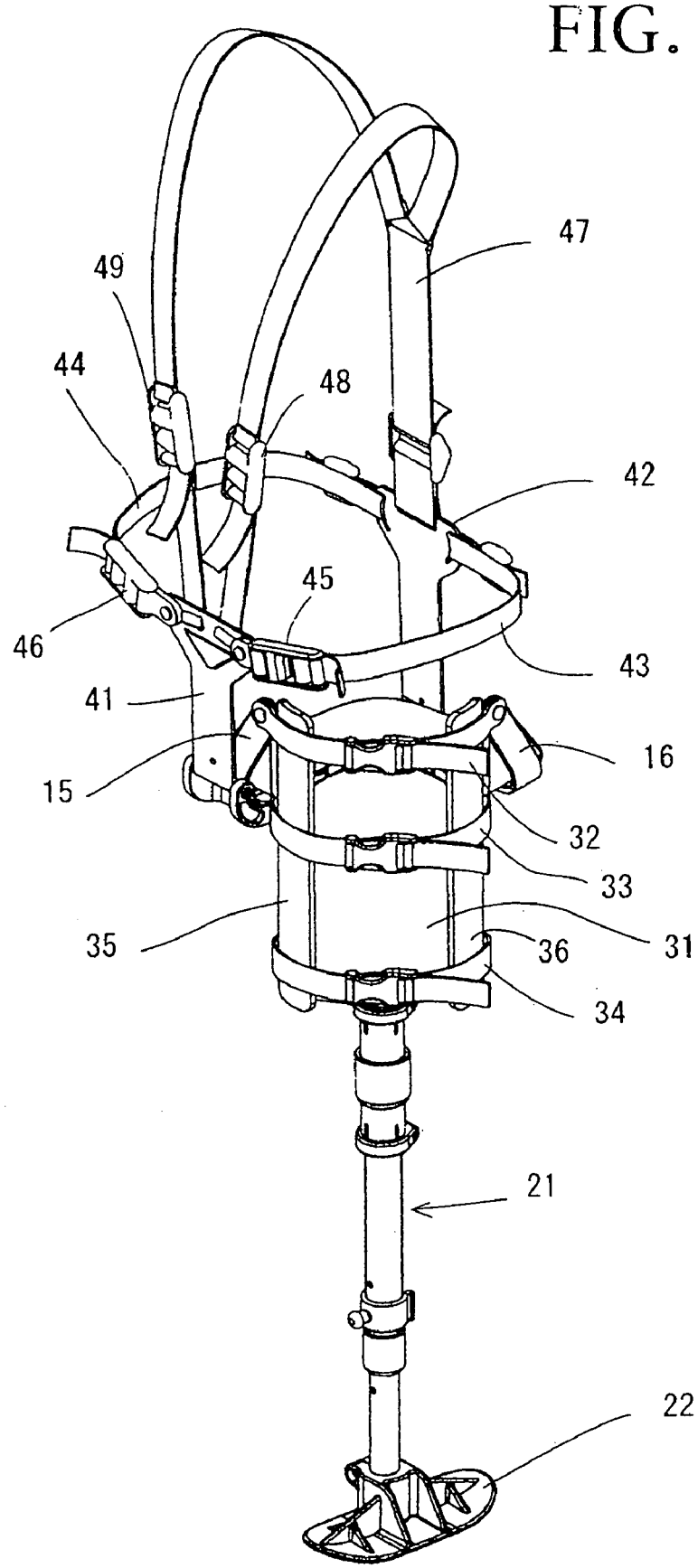
FIG. 16 is a perspective view for showing the hucklebone supporting type artificial leg of the present invention after assembling operation.
Figure 17:
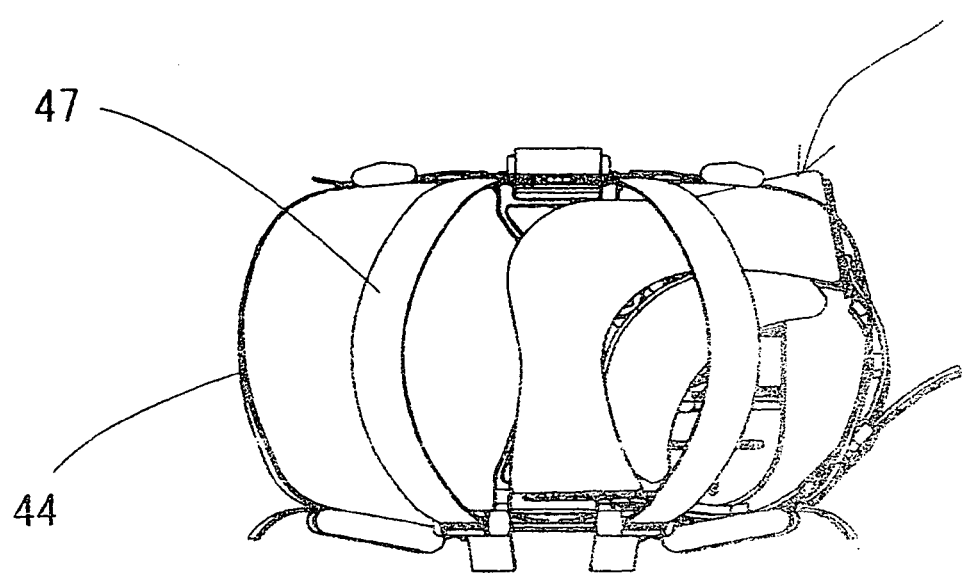
FIG. 17 is a top plan view for showing the hucklebone supporting-type artificial leg of the present invention after assembling operation.
Figure 18:
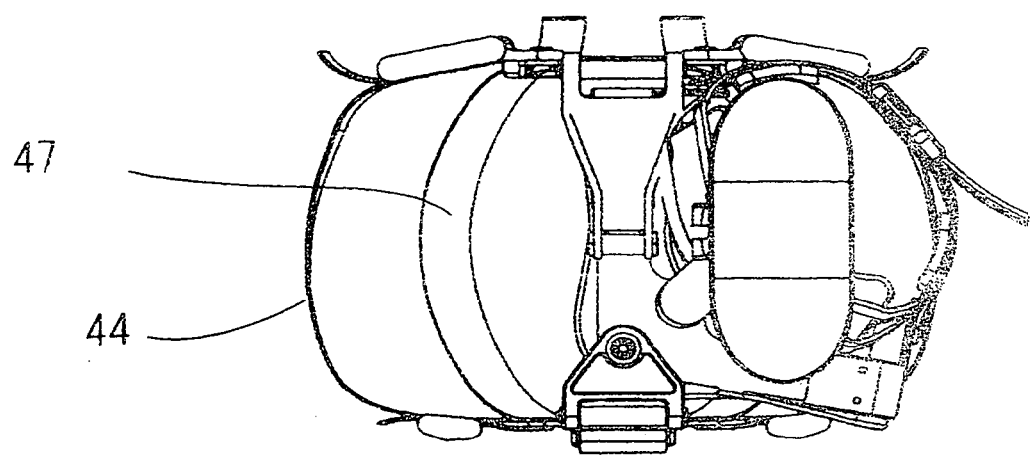
FIG. 18 is a bottom view for showing the hucklebone supporting-type artificial leg of the present invention after assembling operation.
Figure 19:
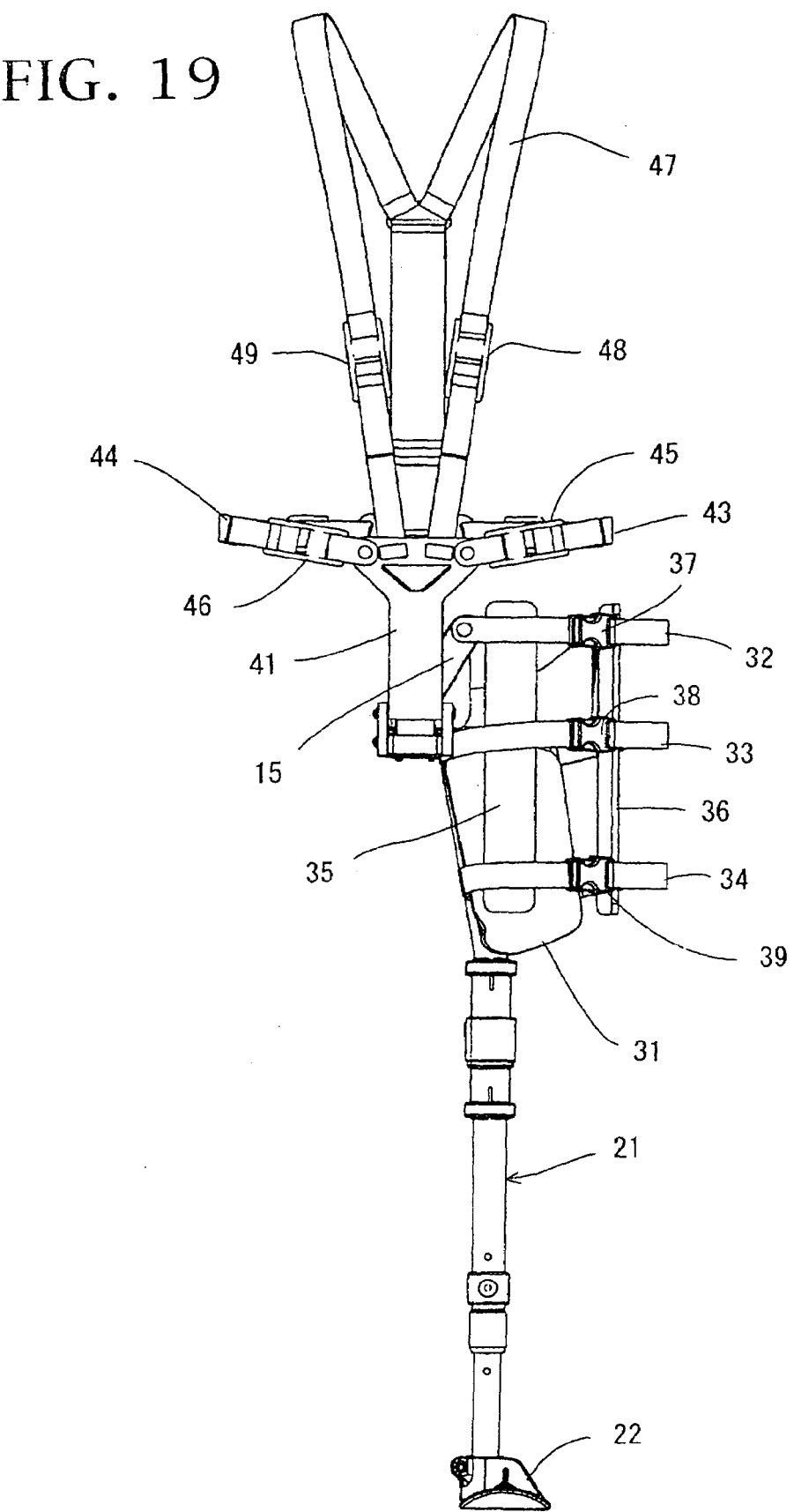
FIG. 19 is a front elevational view for showing the hucklebone supporting-type artificial leg of the present invention after assembling operation.
Figure 20:
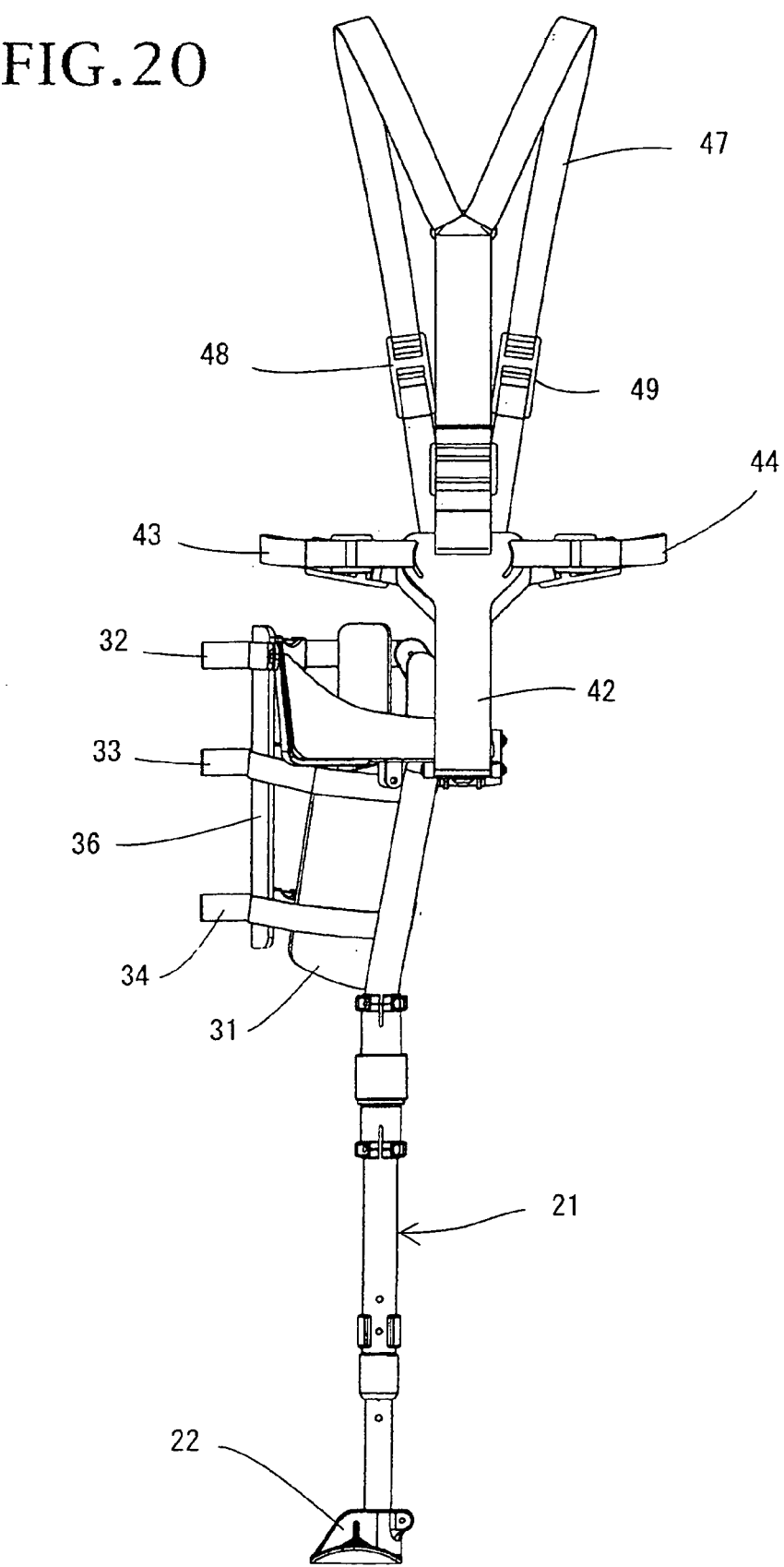
FIG. 20 is a rear view for showing the hucklebone supporting-type artificial leg of the present invention after assembling operation.
Figure 21:
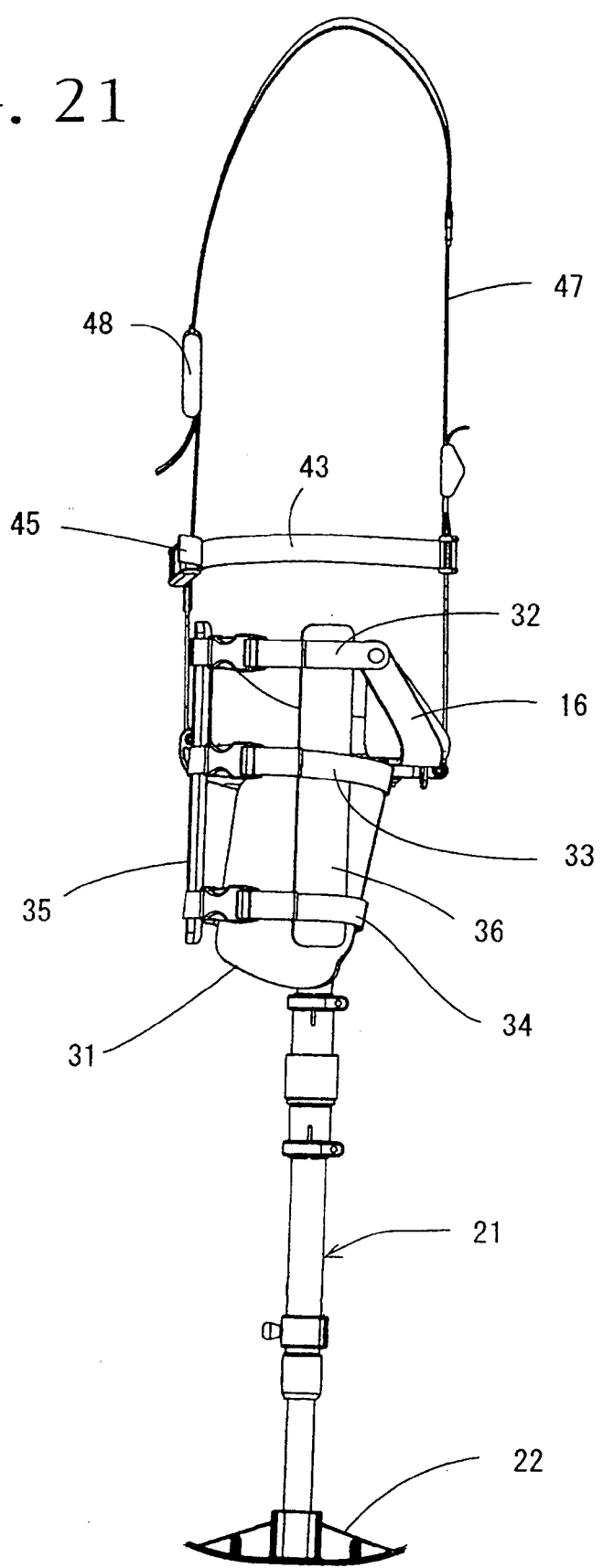
FIG. 21 is a right side elevational view for showing the hucklebone supporting-type artificial leg of the present invention after assembling operation.
Figure 22:
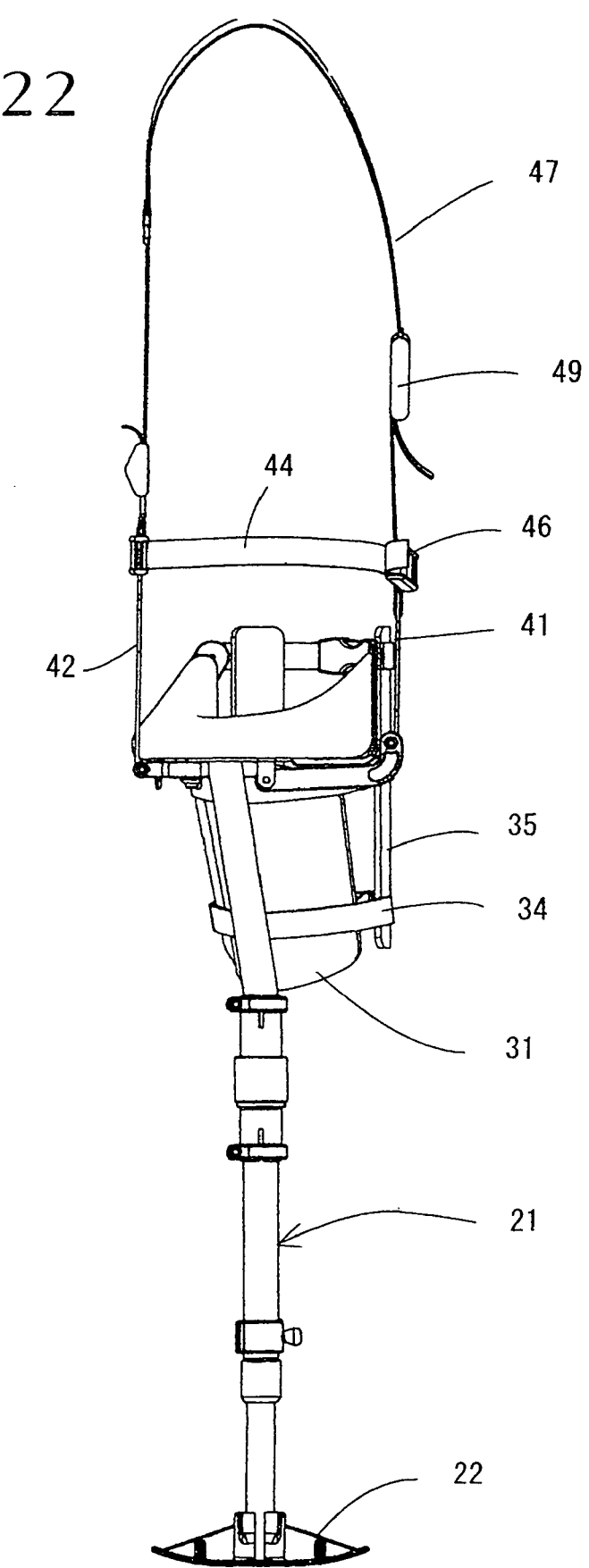
FIG. 22 is a left side elevational view for showing the hucklebone supporting-type artificial leg of the present invention after assembling operation.

Next, the hucklebone supporting-type artificial leg assembled into its wearing state will be described. FIGS. 16 to 22 illustrate the hucklebone supporting-type artificial leg kept in its assembled state. FIG. 16 is a perspective view as seen from a slant front part, FIG. 17 is a top plan view, FIG. 18 is a bottom view, FIG. 19 is a front elevational view, FIG. 20 is a rear view, FIG. 21 is a right side eleventional view, and FIG. 22 is a left side elevational view. As shown in these figures, the thigh-abutting unit 31 is abutted against the left thigh portion at the lost lower leg side of a leg wearing person and the thigh portion is fixed to the thigh-abutting unit 31 with three fastening bands 32 to 34. Both ends of the upper fastening band 32 are connected to the connecting fittings 15, 16 and fastened by a buckle 37 through outside portions of pressing plates 35, 36. The middle fastening band 33 is wound around the rear surface of the thigh-abutting unit 31 and fastened by a buckle 38 through outside portions of the pressing plates 35, 36. The lower fastening band 34 is wound around the back surface of the thigh-abutting unit 31 and fastened by a buckle 39 through outside portions of the pressing plates 35, 36. In this way, since the left thigh portion fixed to the thigh-abutting unit 31 is directed in a slant forward and downward direction, it becomes easy to move the artificial leg in a forward or rearward direction by the left thigh portion during walking.

Next, a waist band 43 is connected to the left sides of the front band supporting unit 41 and the rear band supporting unit 42, and similarly a waist band 44 is connected to their right sides and they are fastened by buckles 45, 46. As a result, the crotch support 1 is tightly fixed at the waist part of the artificial leg wearing person and the person can walk only under this state. In this case, further, a shoulder hanging band 47 is applied between the front band supporting unit 41 and the rear band supporting unit 42 so as to tightly fix the crotch support 1 to the wearing person and the shoulder hanging band 47 is fastened with buckles 48, 49. In this way, a walking characteristic of the person is improved by fixing the crotch support 1 to the wearing person through the waist and both shoulders of the wearing person.

Figure 23:
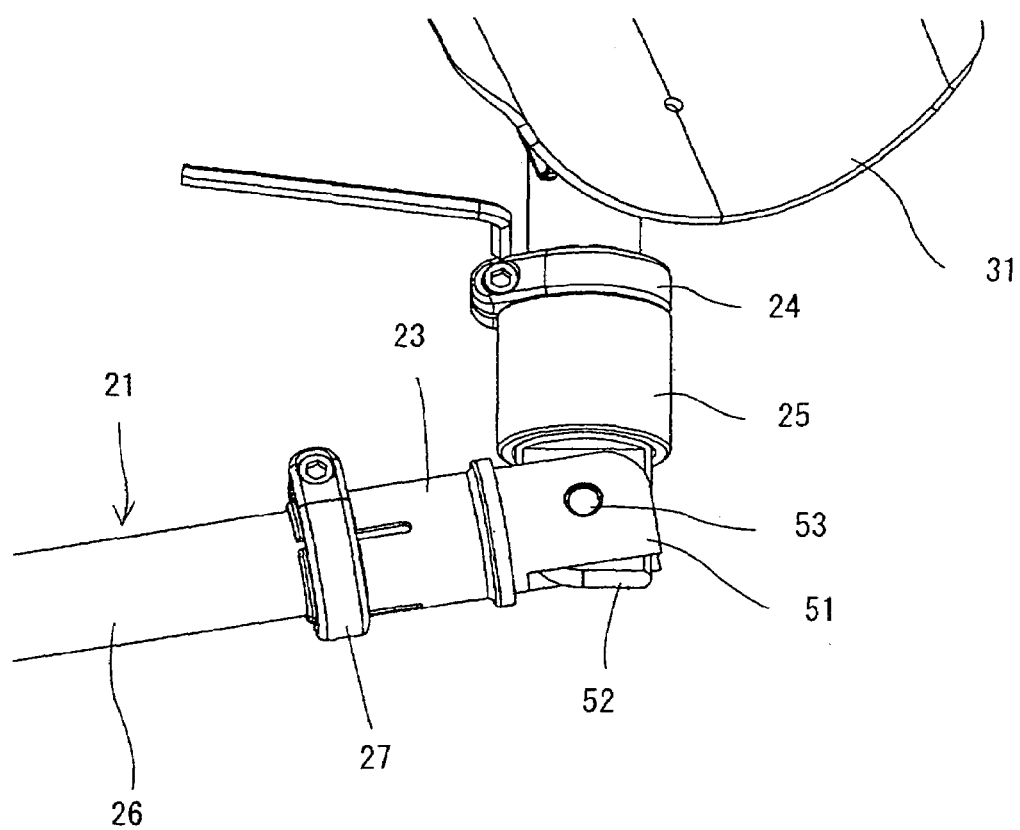
FIG. 23 is a perspective view for showing a bent state of a hinge part formed at an upper shaft.

FIG. 23 is a perspective view for showing a bent state of a hinge unit formed at the midway part of the upper shaft 23. The intermediate part of the upper shaft 23 is divided into an upper segment and a lower segment, slit collars 24, 27 are fixed to the upper and lower portions and a collar 25 is fitted between them in such a way that a collar 25 can be moved up and down. A fork clevis 51 is formed at an upper end below the divided portion, a protrusion 52 corresponding to the fork clevis 51 is formed at a lower end above the divided portion, a pin 53 is inserted into the fork clevis 51 and the protrusion 52 while these fork clevis and protrusion are being fitted to each other, and they are rotatably connected to each other. Usually, the upper shaft 23 is kept under a straight-line rigid state by descending the collar 25 to cover the hinge part under a state in which the hinge part is extended.

The hinge part constructed as described above can be bent by bending the upper part of the upper shaft 23 in a rearward direction after ascending the collar 25 when the artificial leg wearing person interrupts walking and takes a seat at a chair or the like. When the person restarts walking, the hinge part is extended and the collar 25 is slid in a downward direction, the upper shaft 23 becomes a straight line state and the person can walk. In addition, when the person takes a seat while bending the hinge part, the front band supporting unit 41 shown in FIG. 8 can be fallen in a forward and downward direction by the L-shaped link fitting 9 and then a compression at the belly by the front band supporting unit 41 is eliminated when the person takes a seat at a chair or the like.

Figure 24:
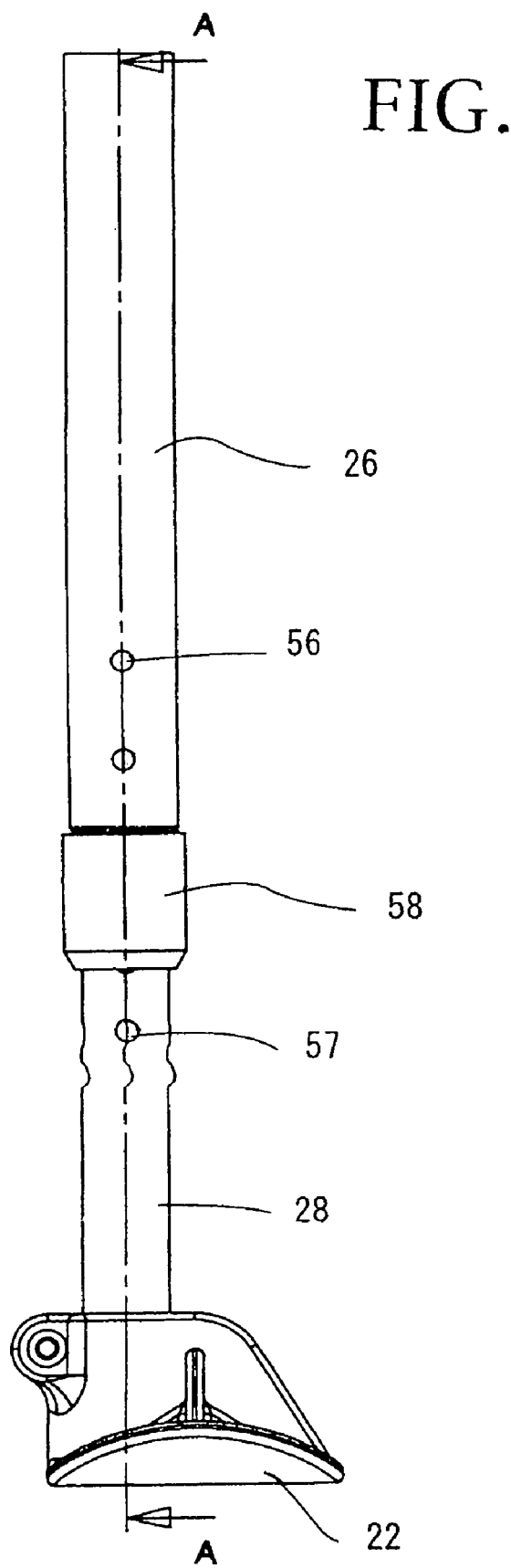
FIG. 24 is an outer appearance view for showing the lower end of a shaft.
Figure 25:
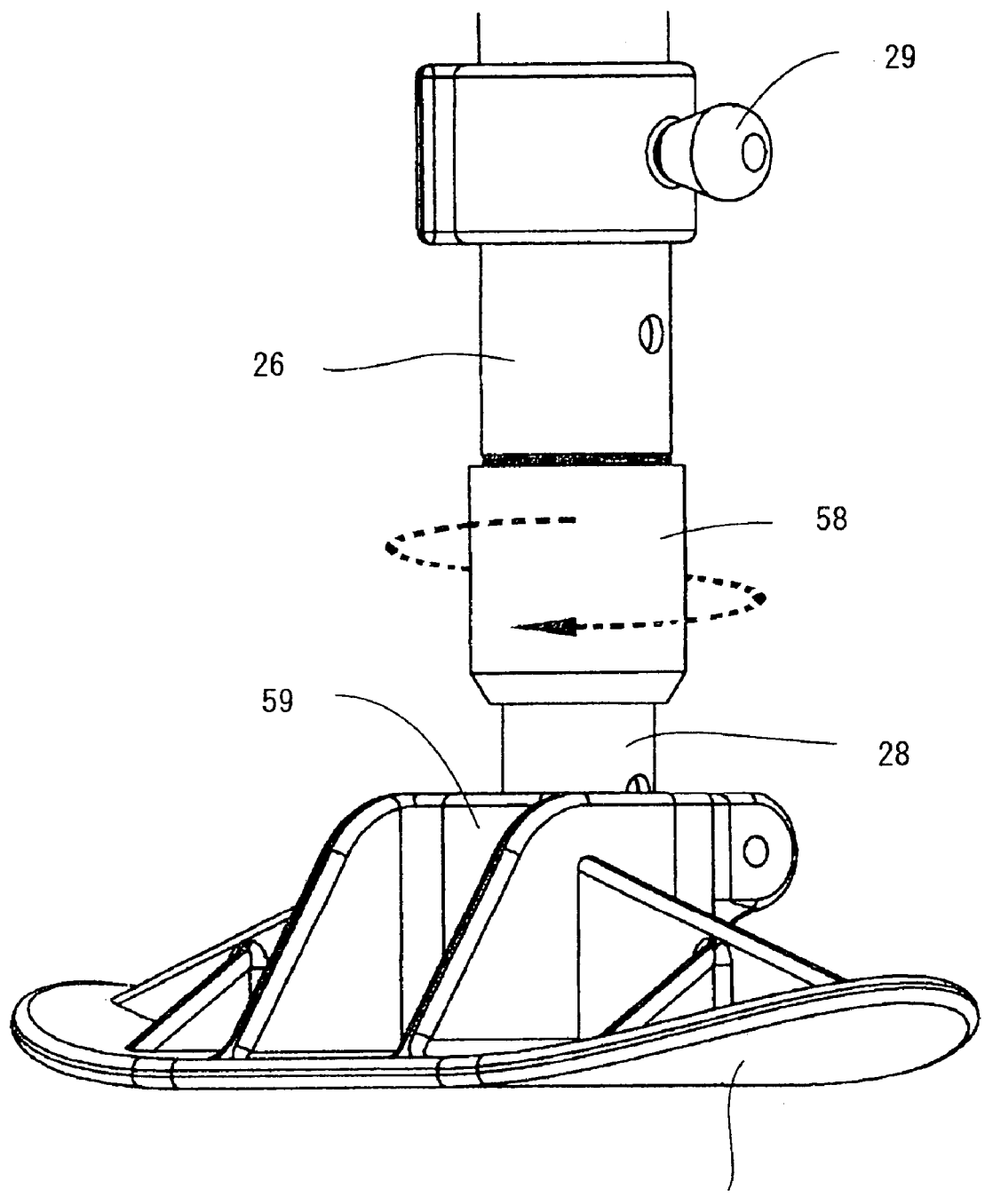
FIG. 25 is an outer appearance view for showing the lower end of a shaft.
Figure 26:
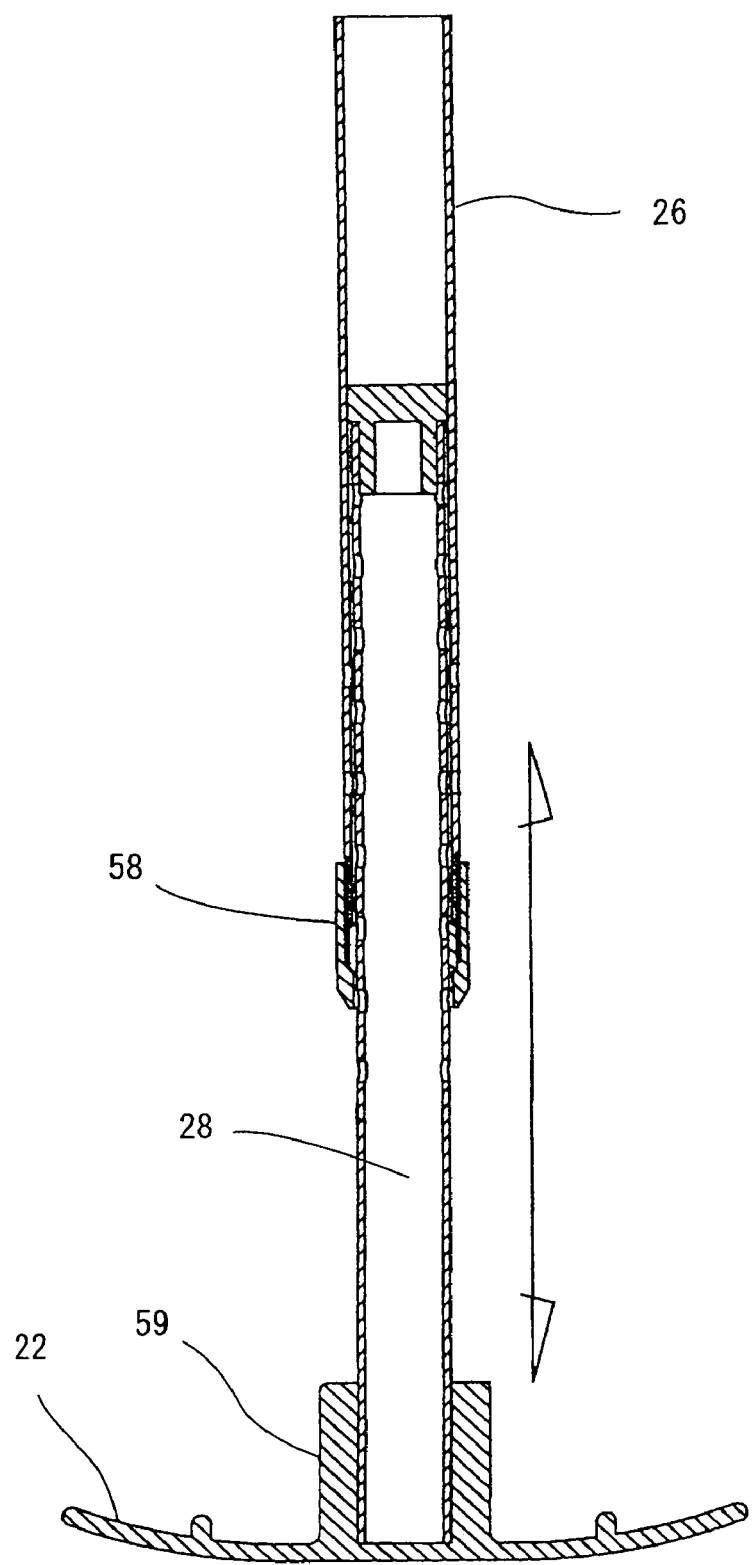
FIG. 26 is a sectional view taken along line A-A of FIG. 24.

FIGS. 24 and 25 are outer appearance views for showing the lower end of the shaft 21. FIG. 26 is a sectional view taken along line A-A of FIG. 24. As shown in the figures, the intermediate shaft 26 is made by a pipe member and the finer lower shaft 28 than the intermediate shaft 26 is inserted inside the lower end in such a way that it can be put in or taken out. The intermediate shaft 26 and the lower shaft 28 are formed with through-pass holes 56, 57 in a specified interval toward their diameter.

A length of the shaft 21 can be adjusted in a stepwise manner by adjusting a fitted amount between the intermediate shaft 26 and the lower shaft 28 and inserting a clip pin 29 into the through-pass holes 56, 57. The clip pin 29 is made such that a pin is fixed at the central portion of a clip made of Ω-shaped resilient member, and the clip pin 29 can be fixed to or removed from the intermediate shaft 26 through a finger-touch operation. The outer circumferential part of the lower end of the intermediate shaft 26 is formed with a thread, a threaded collar 58 is threadably fitted to the former thread and fastened to cause the intermediate shaft 26 and the lower shaft 28 to be connected without any looseness.

In addition, at the lower end of the lower shaft 28 is fixed the foot 22 by fastening the slit formed at the side surface of a hub part 59 with a bolt under a state in which the lower end of the lower shaft is inserted into the hub part 59 protruded at a position offset to one side of the upper surface of the foot 22. Usually, although the center of the foot 22 is offset outside, it is also possible to offset the foot 22 inwardly and the person can walk when the artificial leg wearing person is not familiar with a walking just after wearing the artificial leg. Orientation of the foot 22 is adjusted in compliance with a state in which the shaft 21 is offset to any of the right or left side. In addition, as shown in the bottom views of FIGS.

11 and 18, it is preferable that the foot 22 is set in parallel with a walking direction of the leg wearing person.

Figure 27:
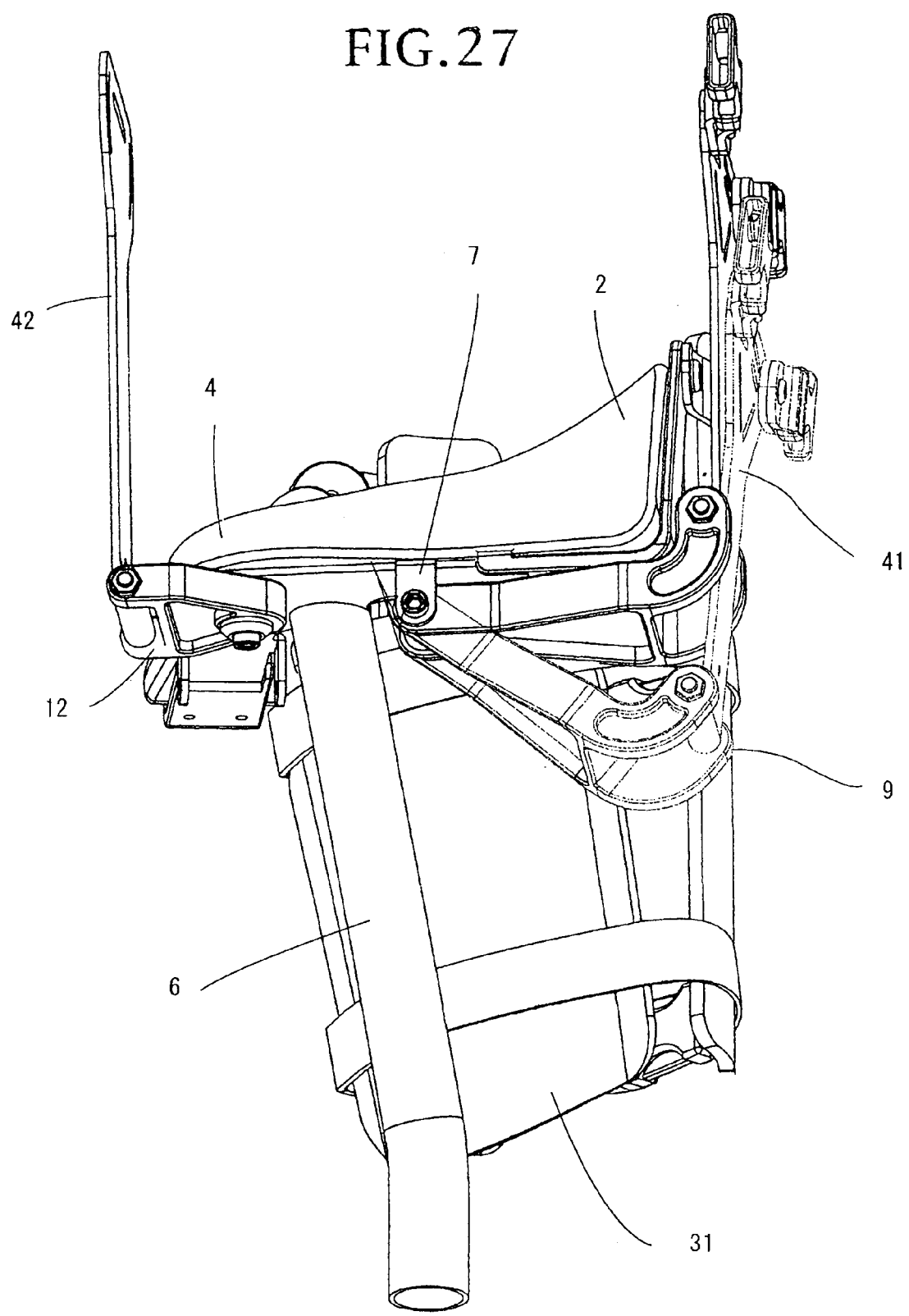
FIG. 27 is a perspective view for showing a movable range of an L-shaped link fitting.

FIG. 27 is a perspective view for showing a movable range of the L-shaped link fitting 9 supporting the front band supporting unit 41. Under a state in which the waist bands 43, 44 are installed at the front band supporting unit 41, the L-shaped link fitting 9 ascends and the inside of the bent part is abutted against the front end 2 of the crotch support 1. Under a state in which the waist bands 43, 44 are removed from the front band supporting unit 41, the L-shaped link fitting 9 descends by its own weight. In addition, when the artificial leg wearing person takes an attitude of taking a seat even under a state in which the waist bands 43, 44 are installed at the front band supporting unit 41, this state becomes a state in which the leg wearing person bends himself forward at the waist part in respect to the artificial leg, so that both the front band supporting unit 41 and the L-shaped link fitting 9 descend.

Figure 28:
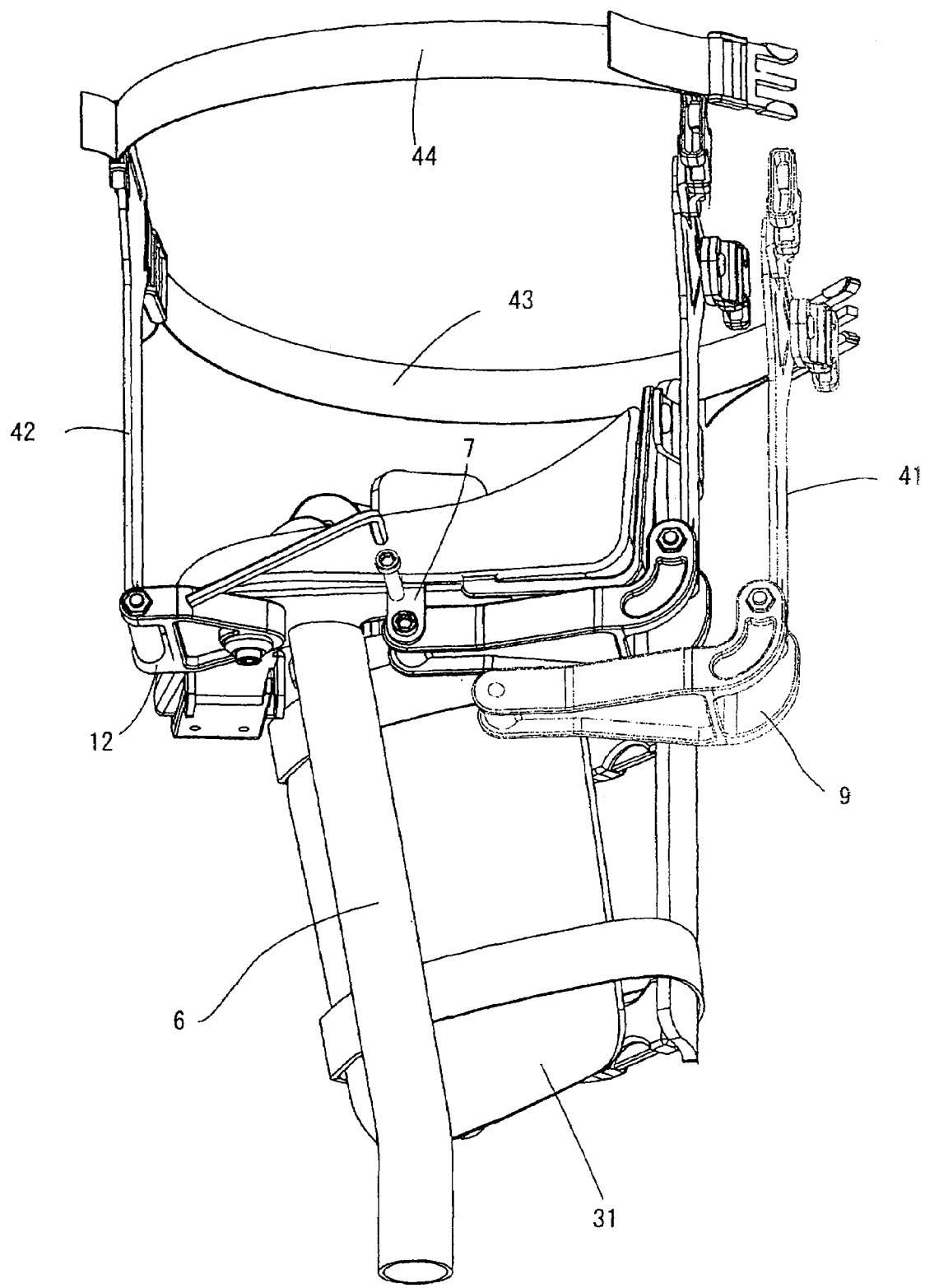
FIG. 28 is a perspective view for showing a fixing or removing operation of an L-shaped link fitting.

FIG. 28 is a perspective view for showing a fixing or removing operation of the L-shaped link fitting 9 supporting the front band supporting unit 41. Although the illustrated example shows a case in which the artificial leg is installed at a person having the left lower leg lost, when the artificial leg is installed at a person having the lost right lower leg, the L-shaped link fitting 9 is removed from the front end 2 of the crotch support 1 and installed at the side end 3. In this case, as shown in the figure, a bolt with a hexagonal hole threadably fitted to the bracket 7 at the lower surface of the crotch support 1 is removed from a hexagonal wrench, the L-shaped link fitting 9 is removed from the bracket 7 and it is installed at the bracket 8 at the side end 3. In this way, replacement of the L-shaped link fitting 9 can be carried out with one hexagonal wrench.

Figure 29:
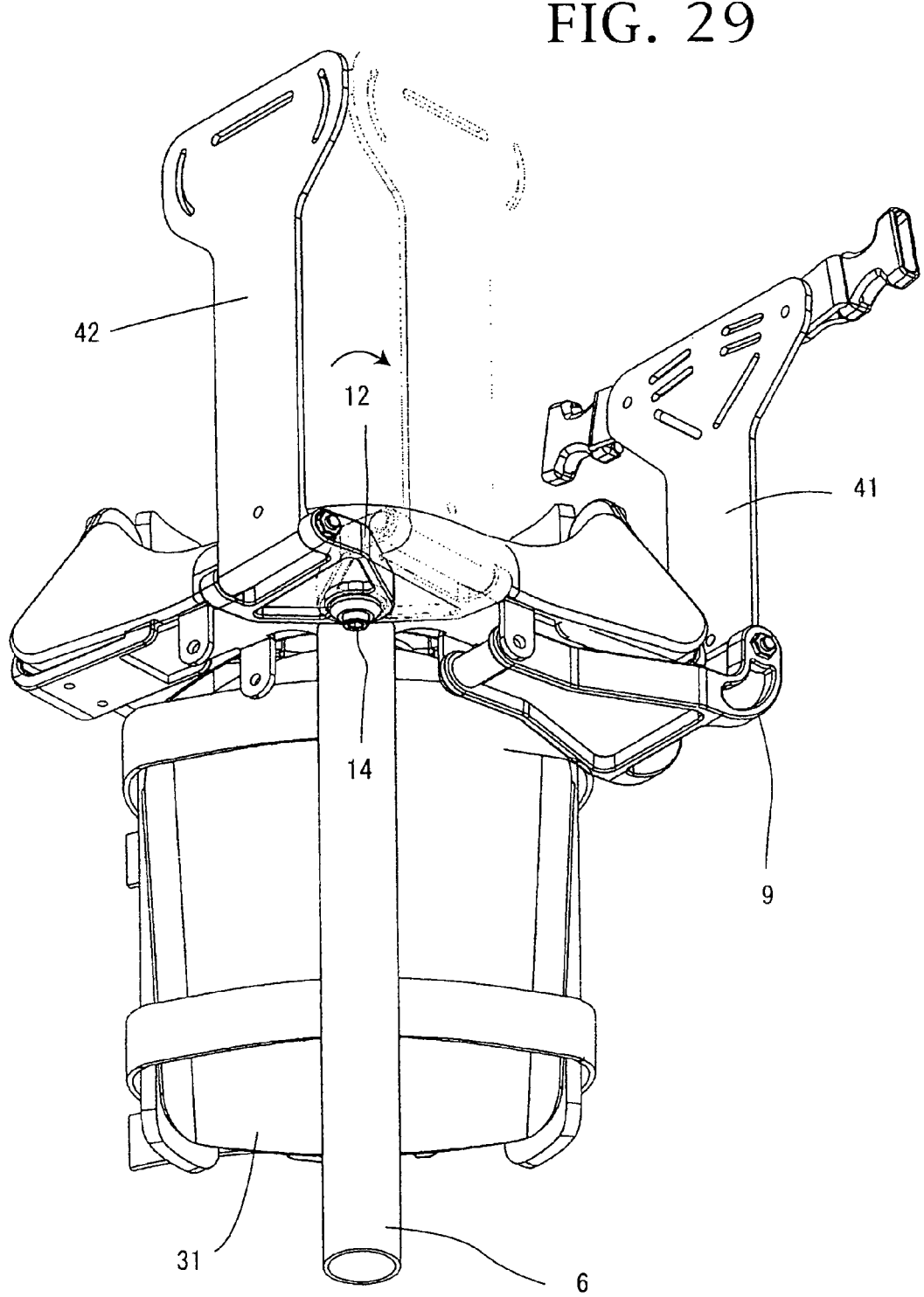
FIG. 29 is a perspective view for showing a case in which a rear band supporting unit is turned and its orientation is changed.

FIG. 29 is a perspective view for showing a case in which an orientation of the rear band supporting unit 42 is turned and changed when the artificial leg is similarly changed over from the left-side wearing mode to the right side wearing mode. Although the illustrated example shows a case in which the artificial leg is installed at a person having the lost left lower leg, when the artificial leg is installed at a person having the lost right leg, the fitting 12 having the rear band supporting unit 42 supported thereat is turned around the small screw 14 in a counter-clockwise direction by about 100 degrees in concurrent with a replacement of the L-shaped link fitting 9. Turning of this fitting 12 can be easily performed without using any tool.

Figure 30:
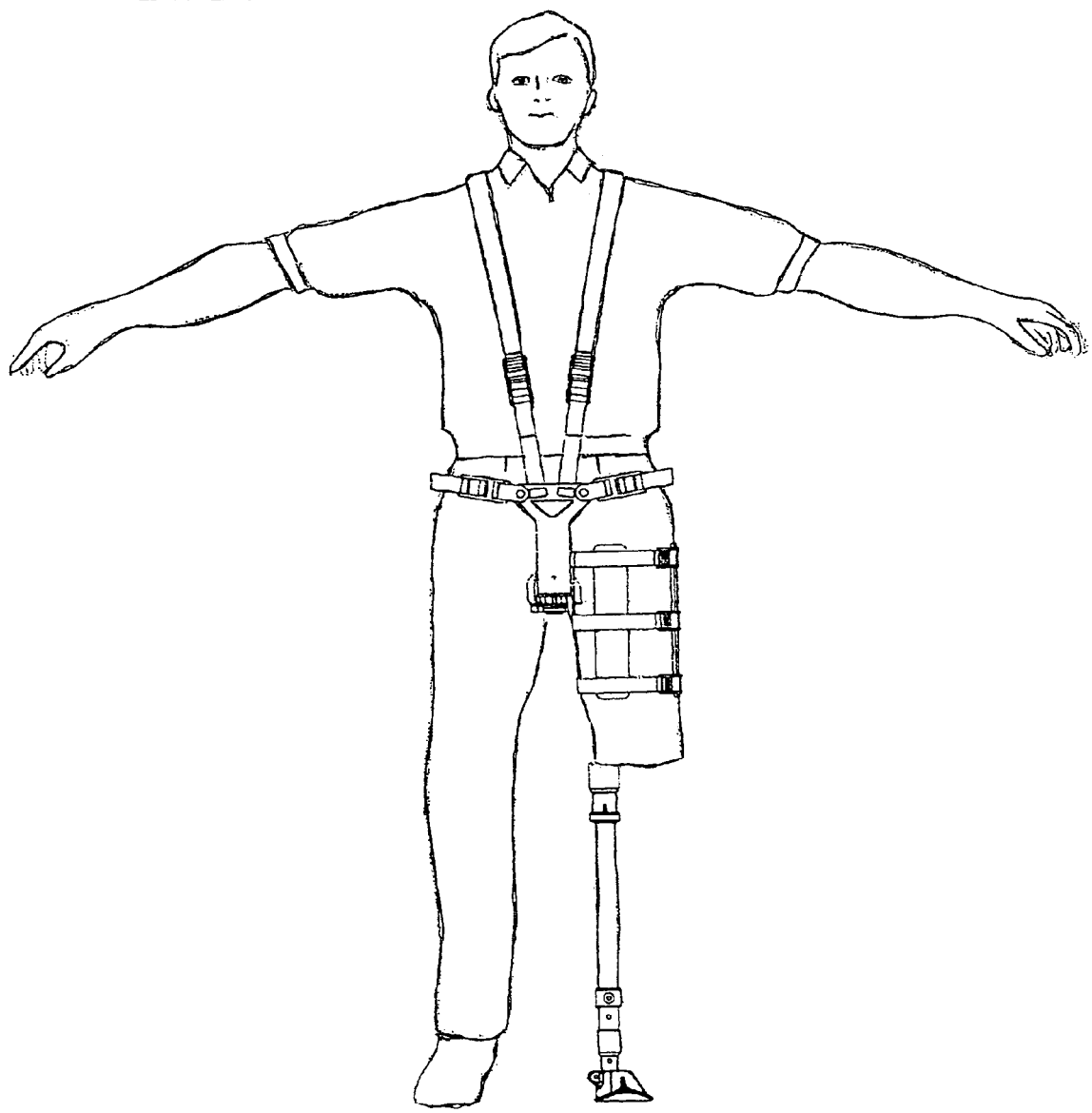
FIG. 30 is a front elevational view for showing a state in which an artificial leg is installed.

FIG. 30 is a front elevational view for showing a state in which the artificial leg having the aforesaid configuration is installed at a person. The crotch support 1 of the artificial leg is abutted against both the crotch part and the left hip at the lost lower leg of the artificial leg wearing person and the artificial leg is fixed to a wearing person by the waist bands 43, 44 and the shoulder hanging band 47 through the front band supporting unit 41 and the rear band supporting unit 42. Further, the left thigh portion is fixed to the thigh-abutting unit 31 with the fastening bands 32 to 34. Since such an installation as above causes a weight of the person applied to the left artificial leg to be supported by the crotch part and the left side hucklebone, a stability in a lateral direction is increased more than the prior art hucklebone supporting-type artificial leg. In addition, during walking, the artificial leg can be moved forward or rearward by the remained left thigh portion and its walking characteristic is improved. In addition, application of the waist bands 43, 44 and the shoulder hanging band 47 enables a wearing characteristic of the leg to a physical body to be increased and also the person to walk while wearing a trouser over the artificial leg under this state, thereby enabling a sense of shame generated at the wearing person due to the artificial leg to be relieved.

The invention claimed is:

1. A hucklebone supporting-type artificial leg comprising a crotch support, a shaft vertically arranged at the lower surface of said crotch support and having substantially the same length as that of a lower leg and a foot attached to the lower end of said shaft characterized in that said crotch support is formed from a first portion and second portion and an intermediate portion between the first portion and the second portion to define a substantially L-shape as seen from its top plan view, the first portion having a respective first portion end and the second portion having a respective second portion end, and the intermediate portion having a respective intermediate portion end, the first portion of said crotch support applied to a substantial part of the front half of the crotch when installed and the second portion of said crotch support applied to a back part at the lost lower leg side and applied to both the hucklebone and the hip at the lost lower leg side when installed, a concave-shaped thigh abutting unit attached to the upper part of said shaft in a slant forward and downward direction and a fastening band for affixing the thigh part at the lost lower leg side to the concave-shaped thigh abutting unit.

2. The hucklebone supporting-type artificial leg according to claim 1 characterized in that said first portion end and said second portion end are raised relative to said intermediate portion.

3. The hucklebone supporting-type artificial leg according to claim 1 characterized in that said shaft is attached at the lower surface of said intermediate portion of said crotch support.

4. The hucklebone supporting-type artificial leg according to claim 1 characterized by comprising a front band supporting unit attached to the first portion end of said crotch support in such a way that it can be turned in frontward, upward and downward directions; a rear band supporting unit attached to the intermediate portion end of said crotch support in such a way that it can be turned in rearward, upward and downward directions; and a waist band connected to each of the upper ends of said front and rear band supporting units and installed around the waist of an artificial leg wearing person.

5. The hucklebone supporting-type artificial leg according to claim 4 further characterized by a shoulder hanging band having having at least first and second ends, one end connected to each of the upper ends of said front and rear band supporting units, the shoulder hanging band installed on the shoulder of an artificial leg wearing person.

6. The hucklebone supporting-type artificial leg according to claim 4 characterized in that said crotch support is formed into a lateral symmetrical shape, said front band supporting unit can be removably installed at both ends of said crotch support, said rear band supporting unit can be installed on a person having the right or left lost lower leg by enabling a fixing orientation at the rear end of the intermediate bent part of said crotch support to be turned around a vertical axis.

7. The hucklebone supporting-type artificial leg according to claim 1 characterized in that said shaft is divided into upper and lower segments having a hinge connected therebetween and a cylindrical member slidably mounted on said shaft for relative sliding movement between an upper position and a lower position, the upper segment pivotable rearwardly when said cylindrical member is in said upper position.

8. The hucklebone supporting-type artificial leg according to claim 1 characterized in that said foot is connected to the lower end of said shaft at an intermediate position in forward and rearward directions of the lower ground contact surface of said foot and also at a position offset to one of the right and left directions and at the same time the lower end of said shaft is inserted into or held at said foot, the foot part is fastened with a screw, and an offset direction of said foot in respect to the lower end of said shaft can be switched over in right and left sides.

* * * * *